US011566260B2

(12) United States Patent
Simoneau et al.

(10) Patent No.: US 11,566,260 B2
(45) Date of Patent: *Jan. 31, 2023

(54) POTENTIATING AGENTS FOR PROTECTING PLANTS FROM FUNGAL INFECTIONS

(71) Applicant: UNIVERSITE D'ANGERS, Angers (FR)

(72) Inventors: Philippe Simoneau, Saint-Clement-de-la-Place (FR); Thomas Guillemette, Avrille (FR); Pascal Richomme, Angers (FR); Jean-Jacques Helesbeux, Angers (FR)

(73) Assignee: UNIVERSITE D'ANGERS, Angers (FR)

( * ) Notice: Subject to any disclaimer, the term of this patent is extended or adjusted under 35 U.S.C. 154(b) by 96 days.

This patent is subject to a terminal disclaimer.

(21) Appl. No.: 16/564,501

(22) Filed: Sep. 9, 2019

(65) Prior Publication Data

US 2020/0002717 A1 Jan. 2, 2020

Related U.S. Application Data

(63) Continuation-in-part of application No. 14/414,788, filed as application No. PCT/EP2013/063574 on Jun. 27, 2013, now Pat. No. 10,405,550.

(30) Foreign Application Priority Data

Jul. 16, 2012 (EP) ..................................... 12176613

(51) Int. Cl.
*A01N 65/00* (2009.01)
*A01N 63/30* (2020.01)
*C12N 15/82* (2006.01)

(52) U.S. Cl.
CPC ......... *C12N 15/8282* (2013.01); *A01N 63/30* (2020.01); *A01N 65/00* (2013.01)

(58) Field of Classification Search
CPC .... C12N 15/8282; A01N 63/30; A01N 65/00; A01N 65/08; A01N 43/90
See application file for complete search history.

(56) References Cited

U.S. PATENT DOCUMENTS

| | | | | |
|---|---|---|---|---|
| 2,844,506 A ‡ | 7/1958 | Jenkins, Jr. | ........... | A61K 31/315 514/494 |
| 5,523,311 A ‡ | 6/1996 | Schurter | .............. | C07D 285/14 514/36 |
| 6,031,153 A ‡ | 2/2000 | Ryals | ....................... | A01N 43/82 435/5 |
| 6,277,416 B1‡ | 8/2001 | Harkrader | .............. | A01N 43/42 424/725 |
| 8,609,084 B2 ‡ | 12/2013 | Pujos | ..................... | A01N 63/04 424/93 |
| 2006/0228428 A1 ‡ | 10/2006 | Kang | .................. | A61K 31/4741 424/72 |
| 2011/0014306 A1 ‡ | 1/2011 | Bombardelli | ...... | A61K 31/4741 424/737 |

FOREIGN PATENT DOCUMENTS

| | | | | |
|---|---|---|---|---|
| DE | 231 482 | | 6/1986 | |
| DE | 231 482 A1 ‡ | | 6/1986 | |
| DE | 242 555 A1 ‡ | | 2/1987 | |
| EP | 0 313 512 | | 4/1989 | |
| EP | 0 313 512 A2 ‡ | | 4/1989 | ............ A01N 43/82 |
| EP | 0 878 129 | | 11/1998 | |
| EP | 0 878 129 A1 ‡ | | 11/1998 | ............ A01N 43/16 |
| EP | 1 358 801 | | 11/2003 | |
| EP | 1 358 801 A1 ‡ | | 11/2003 | ............ A01N 57/12 |
| FR | 2 751 172 | | 1/1998 | |
| FR | 2 751 172 A1 ‡ | | 1/1998 | ............ A01N 43/82 |
| FR | 2 894 771 | | 6/2007 | |
| FR | 2 894 771 A1 ‡ | | 6/2007 | ............ A01N 63/04 |
| WO | 242 555 | | 2/1987 | |
| WO | 98/46078 | | 10/1998 | |
| WO | WO-98/46078 A1 ‡ | | 10/1998 | ............ A01N 37/44 |
| WO | 99/53761 | | 10/1999 | |
| WO | WO-99/53761 A1 ‡ | | 10/1999 | ............ A01N 43/16 |
| WO | 00/32048 | | 6/2000 | |
| WO | WO-00/32048 A1 ‡ | | 6/2000 | ............ A01N 37/16 |
| WO | 01/07034 | | 2/2001 | |
| WO | WO-01/07034 A1 ‡ | | 2/2001 | ........... A61K 31/352 |
| WO | 01/62089 | | 8/2001 | |
| WO | WO-01/62089 A1 ‡ | | 8/2001 | ............ A01N 43/90 |
| WO | 2006/050183 | | 5/2006 | |
| WO | WO-2006/050183 A2 ‡ | | 5/2006 | ......... A61K 49/0043 |

(Continued)

OTHER PUBLICATIONS

Humpherson-Jones, F.M., Studies on the Epidemiology of Alternaria brassicicola in Brassica oleracea Seed Production Crops, 1982, Ann. Applied Biology, vol. 100, pp. 61-71. (Year: 1982).*
M. Kawaguchi, Database WPI Week 199732 Thomson Scientific, London GB ; AN 1997-347341 & JP 9 143013 A (Yaesu Suisan Kagaku Kogyo KK) Jun. 3, 1997, XP-002686837.‡
J M Joubert et al., Abstract of "A beta 1-3 glucan specific to a marine alga, stimulates plant defence reactions and induces a broad range resistance against pathogens", STN CROPU, 1998, XP-002108577.‡
International Search Report, dated Sep. 17, 2013, from corresponding PCT application.‡
H. Kawai, Database WPI Week 199827 Thomson Scientific, London GB ; AN 1998-300818 & JP 9 175919 A, Jul. 8, 1997, XP-002686838.‡

(Continued)

*Primary Examiner* — Monica A Shin
(74) *Attorney, Agent, or Firm* — Nixon & Vanderhye

(57) ABSTRACT

Disclosed is a method for preventing, controlling or treating a fungal infection on a plant. The method includes applying to such plant organ a non-fungicidal amount or a potentiating amount of a composition including a potentiating agent of a plant defense molecule, in association with a phytopharmaceutical vehicle.

14 Claims, 6 Drawing Sheets

(56) References Cited

FOREIGN PATENT DOCUMENTS

| WO | 2006/066974 | | 6/2006 | |
|---|---|---|---|---|
| WO | WO-2006/066974 | A1 ‡ | 6/2006 | ............... C12Q 1/18 |
| WO | 2009/012481 | | 1/2009 | |
| WO | WO-2009/012481 | A1 ‡ | 1/2009 | ............. A01N 63/02 |
| WO | WO-2014012766 | A1 * | 1/2014 | ............. A01N 43/90 |

OTHER PUBLICATIONS

Meizhong Hu et al., Abstract of "Inhibitory effects of macleaya cordata alkaloids on phytophthora parasitica", database accession No. 2010:1323926 & Hu, Meizhong et al.: "Inhibitory effects of macleaya cordata alkaloids on phytophthora parasitica". Heilongjiang Xumu Shouyi, (6), 137-139; Coden: HXSHEF; ISSN: 1004-7034, 2010.‡

Baerbel Kaestner et al., Abstract of "Chitinase in cucumber hypocotyls is induced by geminating fungal spores and by fungal elicitors in synergism with inducers of acquired resistance", 1998, retrieved from Biological database accession No. 186010, XP-002089791.‡

Aymeric Joubert et al., "Laser nephelometry applied in an automated microplate system to study filamentous fungus growth", Biotechniques, 2010, pp. 399-404, vol. 48, No. 5.‡

Liu, H., Isoquinoline Alkaloids from Macleaya cordata Active Against Plant Microbial Pathogens, 2009, Natural Product Communications, vol. 4, No. 11, pp. 1557-1560. (Year: 2009).‡

Martinez, J., Natural Fungicides Obtained from Plants. [online]. Fungicides for Plant and Animal Diseases, Jan. 2012 [retrieved on Apr. 14, 2016], Retrieved from the Internet:<http://cdn.intechopen.com/pdfs/26021/InTech-Natural_fungicides_obtained_from_plants.pdf>, 27 pages.‡

Feng, G., Inhibitory Activity of Dihydrosanguinarine and Dihydrochelerythrine against Phytopathogenic Fungi, Jul. 2011, Natural Product Research, vol. 25, No. 11, pp. 1082-1089.‡

Martinez, J., Natural Fungicides Obtained from Plants, [online]. Fungicides for Plant and Animal Diseases, Jan. 2012 [retrieved on Apr. 14, 2016], Retrieved from the Internet:<http://cdn.intechopen.com/pdfs/26021/InTech-NaturaUungicides_obtained_from_plants.pdf>, 27 pages.

\* cited by examiner
‡ imported from a related application

POTENTIATING AGENTS FOR PROTECTING PLANTS FROM FUNGAL INFECTIONS

FIELD OF INVENTION

The present invention pertains to the protection of crops against fungal infections. The present invention more specifically relates to potentiating agents and compositions comprising the same, useful for protecting plant organs against fungal infections.

BACKGROUND OF INVENTION

Phytopathogenic fungi may affect a variety of plant organs, such as leaves, stems, fruits and seeds. Infected plant fruits are usually unfitted for sale, and an infection of leaves or seeds may alter plant development or germination, causing significant reduction of productivity. Therefore, fungal infections may result in substantial economic losses. The control of fungal infections of crops is thus a major economic issue.

Conventional chemical fungicides commonly used to protect crops against fungal infection present the drawback to be highly pollutant for the environment, especially for soil and water supply. Moreover, these products may be toxic for humans.

Other agents target fungal pathways, such as, for example, metabolic pathways. Sterol biosynthesis inhibitors, such as, for example, triadimenol, have been used to control fungi. Moreover, WO2006/066974 describes the use of methionine synthase inhibitors for the treatment of fungal diseases of crops.

However, such inhibitors present a large spectrum of action, and may thus have an inhibitory effect on fungi naturally present in the soil, thereby inducing a disturbance of soil ecosystem.

There is thus a need for a fungicidal composition specific of fungi attacking a plant of interest, while not impacting fungi of the soil.

In response to a fungal infection, plants synthesize antifungal defense molecules, such as, for example, phytoalexins. The inventors showed that a phytopathogenic fungus may adapt its metabolism to protect itself against the toxic effects of these molecules, especially via the activation of signalization pathways. Developing an inhibitor of said pathways may thus be a promising way for protecting plants without any disturbance of the soil ecosystem.

Moreover, for human health sake, it could be of interest to reduce the amount of fungicide applied on crops. Indeed, as fungicide applied on crops may be found on food, precautionary principle requires minimizing the amount of fungicide used.

The inventors herein identified agents that potentiate the action of plant defense molecules, such as, for example, inhibitors of signalization pathways activated in a phytopathogenic fungus in response to a plant defense molecule. Due to this potentiating effect, it is possible to reduce the amount of fungicide applied on crops.

The present invention thus relates to a composition or product comprising such a potentiating agent. In one embodiment, the invention focuses on destructing fungi when the fungi actually is attacking a plant of interest, while not impacting fungi of the soil, thus avoiding any disturbance of the soil ecosystem.

SUMMARY

As expected, sub-effective concentrations of anti-fungal agencies such as benzo[c]phenantridine alkaloids are not fungistatic or fungicide against plant phytopathogens. However, it was surprisingly found by the inventors that, whilst benzo[c]phenantridine alkaloids in non-fungicidal concentrations do not have a direct effect on the fungal growth, they actually present a synergistic effect with the plant defense mechanisms of the infected plant and are thus effective in the management of plant fungal infections. Therefore, such alkaloids even though they do not have a direct effect on the fungal growth, they potentiate the defense mechanisms of the infected plant, namely the phytoalexins secreted by the plant in response to the fungal infection.

Without willing to be bound by a theory, it is considered that such alkaloids hinder the fungal counter-defense mechanisms that are physiologically activated by the fungi in response to the plant phytoalexins' anti-fungal effect.

Therefore, according to a first aspect, the present invention relates to a method for preventing, controlling or treating a fungal infection on a plant organ comprising applying to said plant organ a composition comprising at least one potentiating agent selected from chelerythrine, sanguinarine; and $Cl^-$, $HSO_4^-$, $I^-$, $HCO_3^-$ salts thereof at a concentration equal or inferior to the non-fungicidal concentration molecule, in association with a phytopharmaceutical vehicle. The non-fungicidal concentration of such at least one potentiating agent is determined by comparing the growth of the phytopathogenic fungal strain cultures in contact with increasing concentrations of said at least one potentiating agent, with the growth of a control culture of the phytopathogenic fungal strain, in the absence of said at least one potentiating agent; the last concentration of the increasing concentrations of the at least one potentiating agent resulting in the same fungal culture growth as the control culture being determined as the non-fungicidal concentration of said at least one potentiating agent.

In one embodiment, the non-fungicidal amount of at least one potentiating agent is carried-out by spectrophotometry or nephelometry.

In one embodiment, the phytopathogenic fungal infection is an infection by a phytopathogenic fungus selected from the genera *Alternaria, Sclerotinia* and *Venturia*.

In one particular embodiment, the fungal infection is an infection by a phytopathogenic fungus selected from the group comprising *Alternaria brassicicola, Alternaria dauci* and *Venturia inaequalis*.

The inventors have particularly shown that phytoalexins, namely indolic phytoalexines such as camalexin or brassinin, or phenolic phytoalexines such as 6-methoxymellein or apple phytoalexins are potentiated by the method of the invention. Such phytoalexins are generally secreted by plants of the Brassicacae, Apiaceae, Vitaceae and Rosaceae families.

Thus, in one particular embodiment, the plant organ to be treated is of a plant belonging to the Brassicacae, Apiaceae, Vitaceae and Rosaceae families.

In yet another particular embodiment, the plant organ to be treated is of a plant selected from *Brassica carinata, Brassica juncea, Brassica oleracea, Brassica napus, Brassica nigra* and *Brassica rapa*.

In specific embodiments of the invention, the plant organ, the phytopathogenic fungus (Phytopathogenic system) and the non-fungicidal concentration of the at least one potentiating agent in the applied composition is selected from the following combinations presented in table A.

| Plant organ belonging to: | Phytopathogenic fungus to be treated: | Applied non-fungicidal concentration |
|---|---|---|
| Brassicaceae family | *Alternaria* genus | 1-25 µM |
| Apiaceae family | *Alternaria* genus | 1-10 µM |
| Rosaceae family | *Venturia* genus | 1-5 µM |
| Brassicaceae family | *Alternaria brassicicola* | 1-25 µM |
| *Daucus carota* | *Alternaria dauci* | 1-10 µM |
| *Malus domestica* | *Venturia inaequalis* | 1-5 µM |

Table A presenting particular phytopathogenic systems with the respective non-fungicidal concentrations of the at least one potentiating agent according to the invention.

In one specific embodiment, the plant organ belongs to *Brassica oleracea* plant, said phytopathogenic fungus being *Alternaria brassicicola*, and said non-fungicidal concentration of the at least one potentiating agent in the applied composition being from 1 to 25 µM.

According to an alternative implementation of the method, the applied composition further comprises a plant defense molecule selected from brassinin, camalexin, resveratrol, 3,5-dihydroxybiphenyl, aucuparin and 6-methoxymellein.

In one embodiment, the applied composition further comprises an agent for stimulating the production of a plant defense molecule such as acibenzolar-S-methyl, chitosan, laminarin, *Reynoutria sachalinensis* extract, calcium prohexadione, harpine, yeast wall extracts, oligogalacturonides and calcium phosphite.

According to further embodiments of the method, the applied composition may further comprise an insecticide and/or a herbicide.

According to a second aspect, the invention relates to a phytosanitary or phytopharmaceutical composition to be applied onto a plant organ and which is suitable for preventing, controlling or treating a plant infection by a phytopathogenic fungus. Such composition comprises at least one potentiating agent selected from chelerythrine, sanguinarine; and $Cl^-$, $HSO_4^-$, $I^-$, $HCO_3^-$ salts thereof, in a concentration equal or inferior to the non-fungicidal concentration against a phytopathogenic fungal strain. As previously discussed, the non-fungicidal concentration of the at least one potentiating agent is phytopathogenic fungus-dependent. Thus, the concentration of the at least one potentiating agent in the composition is determined in vitro, as previously presented.

In one embodiment, the phytosanitary or phytopharmaceutical composition according to the invention:
   comprises the at least one potentiating agent in a concentration equal or inferior the non-fungicidal concentration towards a phytopathogenic fungus, and
   is suitable for treating particular phytopathogenic systems
   both the concentration of the at least one potentiating agent and the phytopathogenic system being defined in table A.

In one embodiment, the composition further comprises a plant defense molecule selected from brassinin, camalexin, resveratrol, 3,5-dihydroxybiphenyl, aucuparin and 6-methoxymellein.

In one embodiment, the composition further comprises an agent for stimulating the synthesis of a plant defense molecule as previously described and/or a phytopharmaceutical vehicle.

In a last aspect, the invention also relates to a seed coated, dressed or pelleted with a composition of the invention.

Definitions

In the sense of the present invention, the following terms have the following meanings:

"Alkyle": any saturated linear or branched hydrocarbon chain, with 1 to 12 carbon atoms, preferably 1 to 6 carbon atoms, and more preferably methyl, ethyl, propyl, isopropyl, n-butyl, sec-butyl, isobutyl and tert-butyl.

"Alkenyl": any linear or branched hydrocarbon chain having at least one double bond, of 2 to 12 carbon atoms, preferably 2 to 6 carbon atoms, and more preferably methylene, ethylene, propylene, isopropylene, n-butylene, sec-butylene, isobutylene and tert-butylene.

"Alkylsufonate": any $O-SO_2$-alkyl group.

"anti-fungal agent": refers to a phytopharmaceutical agent that can either be fungicide or fungistatic. In one embodiment, the antifungal agent is a synthetic or inorganic fungicide or fungistatic. In one embodiment, the antifungal agent is selected from plant defense molecules. In one embodiment, the antifungal agent is a synthetic fungicide or fungistatic agent selected from agents for stimulating the production of a plant defense molecule.

"Alkaloid": refers to a large group of naturally occurring compounds comprising basic nitrogen atoms. Examples of alkaloids include, but are not limited to, isoquinoline derivatives, indole derivatives, pyridine derivatives, pyrrolidine derivatives, tropane derivatives, pyrrolizidine derivatives, piperidine derivatives, quinolizidine derivatives, indolizidine derivatives, oxazole derivatives, isoxazole derivatives, thiazole derivatives, isothiazole derivatives, quinazoline derivatives, acridine derivatives, quinolone derivatives, imidazole derivatives and purine derivatives.

"Ring" refers to a cyclic molecular arrangement of 4 to 20 atoms, preferably of 5 or 6 atoms. The ring may be an homocycle, where all atoms are carbons, or an heterocycle, where at least one atom is not carbon, and preferably is N, O or S.

"Plant defense molecule" refers to a molecule belonging to the immune system of the plant and used by a plant organ to resist to an aggression, such as, for example, a fungal infection. A plant defense molecule may thus be toxic for the phytopathogenic fungus infecting the plant organ. In one embodiment, a plant defense molecule is a molecule whose synthesis is not constitutive (i.e. the molecule is not synthesized at a constant level by the plant organ) but is induced by an aggression or an elicitor (inducer of pathogen resistance). In one embodiment, said plant defense molecule is a phytoalexin.

"Non-fungicidal amount" represents an amount (alternatively expressed as concentration) necessary to alter and/or inhibit the signaling pathways involved in the growth and/or development of fungi, said amount being lower than a fungicidal amount.

As used herein, a "fungistatic effect" refers to an inhibiting and/or stopping and/or controlling effect upon the growth and/or development of fungi without destroying them, whereas a "fungicidal effect" refers to the destruction of fungi.

Methods for determining the non-fungicidal amount of a product are well known from the skilled artisan. Examples of such methods include, but are not limited to, growth test in presence of increasing concentrations of said product, which may be carried out in culture in liquid or solid medium.

In one embodiment of the invention, the fungistatic or fungicidal effect is measured after at least 5 hours of culture, preferably at least 10 hours, more preferably at least 20 hours, and even more preferably at least 30 hours.

In one embodiment of the invention, the fungistatic or fungicidal effect is assessed by comparing growth of treated fungi with growth of untreated fungi (controls cultured in the absence of the tested product).

One example of such a method may be the following (Test A):

Suspensions of fungal conidia (starting material being for example $10^5$ conidia/mL) are cultured in liquid medium, such as, for example, 300 µL of PBD medium, on microplate wells at 25° C. with shaking at 175 rpm for 5 minutes every 10 minutes. Increasing concentrations of the tested product are added on wells, and fungal growth is measured, during at least 5 hours, preferably at least 10, 20, 30 hours. Methods for measuring fungal growth are well known from the skilled artisan. Examples of such methods include, but are not limited to, photometry, such as, for example, spectrophotometric methods; or nephelometry, such as, for example, laser nephelometry as described in Joubert et al (Biotechniques, 2010, 48:399-404). Growth inhibition is measured by comparing the Area Under Curves (AUC) of treated samples and of untreated controls. Test A is carried out in Example 1.

"Potentiating agent of a plant defense molecule" refers the at least one potentiating agent belonging to the benzo[c]phenantridine alkaloids according to the invention. In the context of the present invention the at least one potentiating agent or the potentiating agent refers to a compound or an agent which, when associated, in a non-fungicidal amount, with a plant defense molecule has a fungicidal or fungistatic effect; preferably the potentiating agent and the plant defense molecule are both used in a non-fungicidal amount. In the present invention, the potentiating agent is a product capable of altering and/or inhibiting the signaling pathways involved in the growth and/or development of fungi, when applied in a non-fungicidal amount. In an embodiment, the potentiating agent is not selected in the group consisting of a phosphorous acid or a derivative of phosphorous acid; salicylic acid; succinic acid; lactic acid; jasmonic acid; isonicotinic acid; arachidonic acid; dichloroisonicotinic acid; berberin or berberin chloride; a yeast extract or fragment thereof; an algae extract; a glycoconjugate; a polysaccharide, including chitosan; a benzothiadiazole.

In one embodiment, a fungicidal or fungistatic effect means that no fungal growth is measured after 5 hours of culture, preferably after 10, 20, 30, or more hours of culture. In another embodiment, a fungicidal or fungistatic effect means that fungal growth of treated fungi is reduced by at least 50%, preferably at least 60, 70, 80, 90% as compared to untreated fungi or to fungi treated with a non-fungicidal amount of said agent or of said plant defense molecule after 5 hours of culture, preferably after 10, 20, 30, or more hours of culture.

In one embodiment, a potentiating agent of a plant defense molecule is an agent having fungicidal or fungistatic effect when tried in the conditions of Test B.

Test B:
1) Determining a non-fungicidal amount of said agent, preferably according to Test A;
2) Determining a non-fungicidal amount of a plant defense molecule, preferably according to Test A;
3) Measuring growth of fungal conidia in a medium comprising a combination of a non-fungicidal amount of the agent, as determined in step 1, and a non-fungicidal amount of the plant defense molecule, as determined in step 2. In one embodiment, the growth is measured as follows: Suspensions of fungal conidia (starting material: $10^5$ conidia/mL) are cultured in liquid medium, such as, for example, 300 µL of PBD medium, on microplate wells at 25° C. with shaking at 175 rpm for 5 minutes every 10 minutes. Non-fungicidal concentrations of the tested agent and of the tested plant defense molecule are added on wells, and fungal growth is measured during at least 5 hours, preferably at least 10, 20, 30 hours. Methods for measuring fungal growth are well known from the skilled artisan. Examples of such methods include, but are not limited to, photometry, such as, for example, spectrophotometric methods; or nephelometry, such as, for example, laser nephelometry as described in Joubert et al (Biotechniques, 2010, 48:399-404). Growth inhibition is measured by comparing the Area Under Curves (AUC) of treated samples and of untreated controls.

Test B is carried out in Example 1.

In one embodiment, the potentiating agent of a plant defense molecule is a homologous potentiating agent. As used herein, a "homologous" potentiating agent of a plant defense molecule potentiates the effect of the plant defense molecule synthesized by the plant organ to be treated.

In another embodiment, the potentiating agent of a plant defense molecule is a heterologous potentiating agent. As used herein, a "heterologous" potentiating agent of a plant defense molecule potentiates the effect of a plant defense molecule which is not the plant defense molecule synthesized by the plant organ to be treated.

"Potentiating amount" refers to the amount of said potentiating agent, which is non-fungicidal per se, but which, when combined to a plant defense molecule, preferably to a non-fungicidal per se amount of said plant defense molecule, is fungicidal or fungistatic, preferably fungistatic, i.e. it inhibits or stops fungal growth. In one embodiment, the potentiating amount of a potentiating agent of a plant defense molecule is determined according to Test B.

"Synergistic effect": defines the interaction of two or more agents acting together in a positive way to produce an effect in an amount that they could not separately reach. An "additive synergy" defines a synergy wherein the combined effect of the agents is equal to the sum of the effects of each agent alone. When the combined effect is greater than the sum of the effects of each agent operating by itself, the synergy is referred to as a "potentiating effect". In one embodiment, the synergistic effect is an additive synergy. In another embodiment, the synergistic effect is a potentiating effect.

"Phytopathogenic fungi" refers to fungi pathogens for plant organs.

Examples of phytopathogenic fungi include, but are not limited to, fungi belonging to the Ascomycetes and Basidiomycetes classes, such as, for example, fungi of the order of Erysiphales (such as, for example, family Erysiphaceae, genera *Uncinula, Erysiphe, Sphaerotheca*); fungi of the order of Dothideales (such as, for example, family Venturiaceae genus *Venturia*); fungi of the order of Helotiales (such as, for example, family Sclerotiniaceae, genera *Sclerotinia, Monilia/Monilinia, Botrytis/Botryotinia*); fungi of the order of Taphrinales (such as, for example, family Taphrinaceae, genus *Taphrina*); fungi of the order of Pleosporales (such as, for example, family Pleosporaceae, genus *Alternaria*); fungi of the order of Magnaporthales (such as, for example, family Magnaportaceae genus *Magnaporthe-Pyricularia*); fungi of the order of Hypocreales (such as, for example, family Nectriaceae, genus *Fusarium*); fungi of the order of Uredinales (such as, for example, family Pucciniaceae, genus

*Puccinia*); and fungi of the order of Ustilaginales (such as, for example, family Ustilaginaceae, genus *Ustilago*).

In one embodiment, the fungal strains belonging to the genus *Alternaria* are selected from *Alternaria alternata, A. alternantherae, A. arborescens, A. arbusti, A. blumeae, A. brassicae, A. brassicicola, A. burnsii, A. carotiincultae, A. carthami, A. celosiae, A. cinerariae, A. citri, A. conjuncta, A. cucumerina, A. dauci, A. dianthi, A. dianthicola, A. eichhorniae, A. euphorbiicola, A. gaisen, A. helianthi, A. helianthicola, A. hungarica, A. infectoria, A. japonica, A. limicola, A. linicola, A. longipes, A. molesta, A. panax, A. perpunctulata, A. petroselini, A. porri, A. radicina, A. raphani, A. saponariae, A. selini, A. senecionis, A. solani, A. smyrnii, A. tenuissima, A. triticina* and *A. zinnia*.

In the context of the present invention, the phytopathogen system designates the host-pathogen system wherein the pathogen is a phytopathogen fungus capable of infecting a specific plant-host.

"Plant organ" refers to a plant, a part of plant or a plant propagation material. Examples of plant organs include, but are not limited to, whole plants, leaves, stems, fruits, seeds, plants, part of plants, cuttings, tubers, roots, bulbs, rhizomes and the like.

"Phytopharmaceutical vehicle" refers to a vehicle that does not produce an adverse or other untoward reaction when applied on a plant organ. An example of phytopharmaceutical vehicle includes, but is not limited to, water.

"Agent for stimulating the production of a plant defense molecule" or "elicitor" refers to a compound that, when applied on a plant organ, leads to biochemical and/or physiologic cell reactions resulting in the synthesis, or to an increase of the synthesis of a plant defense molecule, such as, for example, phytoalexin. Said agents may also be referred as "natural defense stimulators". Agents for stimulating the synthesis of a plant defense molecule are known in the prior art, and may be of natural (animal, vegetal or mineral) origin, or synthetic. When these agents enter into contact with the organ plant, signaling pathways are activated. The metabolism of the plant if modified and plant defense molecules are synthesized at a non-fungicidal amount.

Examples of said agents of natural origin include, but are not limited to, algae extracts such as, for example, laminarin; and plant extract such as, for example, *Reynoutria sachalinensis* extract.

Other examples of said agents include, but are not limited to, acibenzolar-S-methyl, sulfur-containing amino acids, such as, for example, methionine, cysteine and cystine; D-glucose and mixtures of sulfur-containing amino acids and D-glucose.

"Phytosanitary or phytopharmaceutical product" refers to active substances and preparations containing one or more active substances, intended to protect plant organs against a harmful organism or prevent the action of a harmful organism.

"Preventing" means avoiding occurrence of at least one adverse effect or symptom of a fungal infection.

"Controlling" means stopping the progression of the fungal infection, and preventing its spread across the healthy parts of the plant organ. In one embodiment, the method of the invention results in reducing the incidence a phytopathogenic infection meaning the decrease of the number on infected plant organs in a plant culture. In one embodiment, the method of the invention results in reducing the severity of a phytopathogenic infection, meaning the decrease of the percentage of the infected surface (i.e. decolorized or necrotic surface) relative to the total plant organ surface.

"Treating" means eliminating fungal contamination, i.e. that there is no viable fungus in the plant organ anymore.

"Phytopharmaceutically effective amount" refers to the amount of an agent necessary and sufficient for, without causing significant negative or adverse side effect to the plant organ, (i) preventing a fungal infection, (ii) slowing down or stopping the progression, aggravation or deterioration of one or more symptoms of the fungal infection; (iii) alleviating said symptoms and/or (iv) eliminating fungal contamination.

"Improving the growing characteristics of a plant organ" may manifest in improving the yield and/or vigour of the plant and/or quality of the harvested product from the plant, or the root rating, or emergence, or protein content, or increased tillering, or bigger leaf blade, or less dead basal leaves, or stronger tillers, or less fertilizer needed, or less seeds needed, or more productive tillers, or earlier flowering, or early grain maturity, or less plant verse (lodging), or increased shoot growth, or earlier germination, or any combination of these factors, or any other advantages familiar to a person skilled in the art.

"Dressing", "coating" and "pelleting" all refer to the direct application of one or more product(s) on a plant organ, generally on a seed, in order to facilitate the seedling and to improve the rate of success of the seedling. "Dressing" is the simplest operation, wherein the product or the mix of products is in the form of a powder or of a wet paste. For "coating", the product or the mix of product is associated with a fixative agent, in order to enhance the adherence of the product. "Pelleting" of a seed refers to the application of products in successive layers, wherein each layer confers specific properties to the seed.

"About" preceding a figure means more or less 10% of the value of said figure.

DETAILED DESCRIPTION

The present invention relates to a potentiating agent of a plant defense molecule.

The present invention also relates to a composition comprising a potentiating agent of a plant defense molecule, in association with at least one phytopharmaceutical vehicle. In an embodiment, this composition is ready to be applied on a plant organ or a crop; in this embodiment, the potentiating agent of a plant defense molecule is present in the composition in at least a non-fungicidal amount, preferably in a non-fungicidal amount.

In one embodiment of the invention, the potentiating agent is a homologous potentiating agent of a plant defense molecule. In one embodiment, the composition consists of a homologous potentiating agent of a plant defense molecule.

In another embodiment, the potentiating agent is a heterologous potentiating agent of a plant defense molecule.

In one embodiment of the invention, the potentiating agent is an alkaloid.

In one embodiment of the invention, said alkaloid is an isoquinoline of general formula (I):

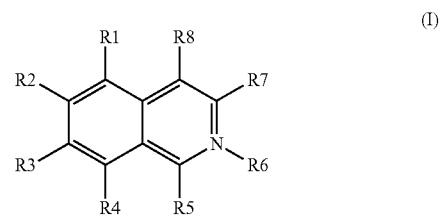

wherein:
each of R1 to R5 independently is H, OH, an alkyl group, an O-alkyl group, a halogen atom or an alkenyl group;
R6 is absent or is present and when present, R6 may be H, OH, an alkyl group, an O-alkyl group or an alkenyl group; when R6 is present, a counterion may be preferably selected from the group comprising Cl⁻, CH₃SO₃⁻, HSO₄⁻, I⁻, HCO₃⁻, BF₄⁻ or PF₆⁻; and
R7 and R8 are independently H, OH, an alkyl group, an O-alkyl group, a halogen atom or an alkenyl group or R7 and R8 form together a ring, preferably a substituted ring, more preferably a substituted or unsubstituted naphthalene, a substituted or unsubstituted isoquinoline.

In one embodiment of the invention, R3 and R4 and/or R6 and R7 and/or R7 and R8, together form a ring, preferably comprising 5 or 6 atoms. In one embodiment, said ring may be substituted.

According to the invention, when the nitrogen atom is in the form of a quaternary ammonium cation, the counterion is preferably selected from the group comprising Cl⁻, CH₃SO₃⁻, HSO₄⁻, I⁻, HCO₃⁻, BF₄⁻ or PF₆⁻.

In one embodiment, the compound of general formula (I) is such that R7 and R8 together form a ring, preferably a substituted ring, more preferably a naphtalene. According to this embodiment, the potentiating agent of a plant defense molecule is a benzo[c]phenantridine of general formula (II):

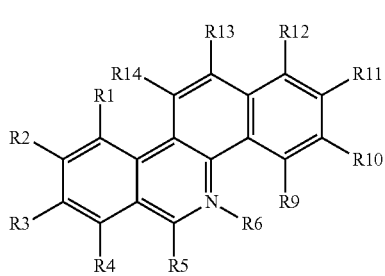

(II)

wherein:
R1 is H, OH, an alkyl group, an O-alkyl group, a halogen atom or an alkenyl group, preferably R1 is H;
R2 is H, OH, an alkyl group, an O-alkyl group, a halogen atom or an alkenyl group, preferably R2 is H or OCH₃;
R3 and R4 are such that
R3 is H, OH, an alkyl group, an O-alkyl group, a halogen atom or an alkenyl group; preferably R3 is OCH₃; and R4 is H, OH, an alkyl group, an O-alkyl group, a halogen atom or an alkenyl group, preferably R4 is H or OCH₃; or
R3 and R4 together form a ring comprising 5 or 6 atoms, preferably a heterocycle comprising 5 or 6 atoms, more preferably a dioxolane;
R5 is H, OH, an alkyl group, an O-alkyl group, a halogen atom or an alkenyl group, preferably R5 is H;
R6 is absent or is present and when present, R6 may be H, OH, an alkyl group, an O-alkyl group or an alkenyl group, preferably R6 is absent or CH₃; when R6 is present, a counterion may be preferably selected from the group comprising Cl⁻, CH₃SO₃⁻, HSO₄⁻, I⁻, HCO₃⁻, BF₄ or PF₆;
R9 is H, OH, an alkyl group, an O-alkyl group, a halogen atom or an alkenyl group, preferably R9 is H;
R10 and R11 are such that
R10 is H, OH, an alkyl group, an O-alkyl group, a halogen atom or an alkenyl group, preferably R10 is OCH₃; and R11 is H, OH, an alkyl group, an O-alkyl group, a halogen atom or an alkenyl group, preferably R11 is OCH₃⁻; or
R10 and R11 together form a ring comprising 5 or 6 atoms, preferably a heterocycle comprising 5 or 6 atoms, more preferably a dioxolane;
R12 is H, OH, an alkyl group, an O-alkyl group, a halogen atom or an alkenyl group, preferably R12 is H;
R13 is H, OH, an alkyl group, an O-alkyl group, a halogen atom or an alkenyl group, preferably R13 is H or O—CH₂—C₆H₅; and
R14 is H, OH, an alkyl group, an O-alkyl group, a halogen atom or an alkenyl group, preferably R14 is H.

Examples of compounds of general formula II include, but are not limited to:

| Compound | Structure |
| --- | --- |
| 1 | ![structure 1] |
| 2 | ![structure 2] |
| 3 | ![structure 3] |
| 4 | ![structure 4] |
| 5 | ![structure 5] |

| Compound | Structure |
|---|---|
| Chelerythrin | (structure: chelerythrine with H$_3$CO, OCH$_3$, N$^+$–CH$_3$, methylenedioxy) |
| Sanguinarin | (structure: sanguinarine with two methylenedioxy groups, N$^+$–CH$_3$) |

In one embodiment, the at least one potentiating agent is selected from chelerythrine, sanguinarine; and Cl$^-$, HSO$_4^-$, I$^-$, HCO$_3^-$ salts thereof. In one embodiment, the at least one potentiating agent is a mixture of chelerythrine and sanguinarine. In one embodiment, the at least one potentiating agent is a mixture of Cl$^-$, HSO$_4^-$, I$^-$, HCO$_3^-$ salts of sanguinarine and chelerythrine.

In one embodiment, the at least one potentiating agent is assessed for its anti-fungal effects as well as comprised in the compositions of the invention in a purified form comprising substantially exclusively such potentiating agent (at least 85 w/w or at least 90% w/w, in weight relative to the potentiating agent composition).

In one embodiment, the at least one potentiating agent is assessed for its anti-fungal effects as well as comprised in the compositions of the invention in the form of a plant extract comprising at least 20% w/w of chelerythrine, sanguinarine; and Cl$^-$, HSO$_4^-$, I$^-$, HCO$_3^-$ salts thereof, in weight relative to the dry weight of the extract. In one embodiment, the extract comprising the at least one potentiating agent is an extract of a plant selected from *Macleaya cordata*, *Chelidonium majus*, *Agremone Mexicana* or *Sanguinaria canadensis*.

In one embodiment, such extract is an aqueous extract, an hydroalcoholic extract, an ethanolic extract, a methanolic extract, an ethyl acetate extract or a supercritical CO$_2$ extract.

In one embodiment, the extract is a crude extract, without subsequent fractionation of the extracted compounds.

In one embodiment, the extract is an enriched extract, preferably an alkaloid-enriched extract or fraction. Numerous techniques are known in the art for obtaining such enriched extract such as for example, liquid-liquid extraction/partitioning or adsorption/absorption chromatography.

In one particular embodiment, the at least one potentiating agent is a *Macleaya cordata* extract. Preferably such extract comprises at least 30% w/w or at least 40% w/w of sanguinarine, in weight relative to the dry extract weight.

In one embodiment, the molar ratio of sanguinarine/chelerythrine is such extract ranges from 2 to 4, from 2.5 to 3.5 or is about 2.8.

The present invention also relates to a potentiating agent capable of altering or inhibiting of the molecular mechanisms activating the growth/development of the phytopathogenic fungi.

In one embodiment of the invention, the potentiating agent is an inhibitor of a signalization pathway activated in a given phytopathogenic fungus, said activation being for example in response to an exposure to a plant defense molecule.

As used herein, a "signalization pathway" refers to a network of proteins acting together to control one or more cell functions. After the first molecule of the pathway has received a signal, it activates another molecule. This process is repeated until the last molecule is activated and the cell function involved is carried out. One example of signalization pathway includes as a first molecule a transmembrane receptor, then a set of kinases, and at last a transcription factor.

Accordingly, an "inhibitor of a signalization pathway" is a compound that limits, prevents or stops the activation of anyone of the proteins of a signalization pathway, resulting in the incapacity of the pathway to control the cell function it usually controls. Referring to the example of the preceding paragraph, an inhibitor may act, without limitation, on the transmembrane receptor (for example, the inhibitor may be an agonist of said receptor), on the catalytic activity of a kinase (for example, the inhibitor may be a catalytic inhibitor of the enzymatic activity of the kinase) or may prevent the action of the transcription factor.

The term "a signalization pathway activated" refers to a signalization pathway wherein the first molecule has received a signal leading to the activation of the other proteins of the network. Methods for determining if a signalization pathway is activated in response to the exposure of a particular molecule are well known from the skilled artisan, and may be carried out on cultures of fungus. Examples of said methods include, without limitation, analysis of the phosphorylation status of kinases of the pathway (for example by Western Blot) or analysis of a reporter gene placed under the control of a promoter specific of the transcription factor. In one embodiment, the expression of the reporter gene is assessed by RT-PCR or RT-qPCR. In another embodiment, the expression of the reporter gene induces visually identifiable characteristics to a cell. Examples of such reporter genes include, but are not limited to, genes encoding fluorescent or luminescent proteins, such as, for example, GFP or luciferase. Another example of a reporter gene is the gene encoding the beta-galactosidase enzyme, whose expression may be easily visualized on culture medium comprising an uncolored substrate analog that is transformed by the enzyme in a colored product.

In one embodiment of the invention, the signalization pathway activated in the phytopathogenic fungus in response to an exposure to a plant defense molecule is the CWI, the HOG and/or the UPR pathway, and the inhibitor used in the present invention is thus an inhibitor of the CWI, the HOG and/or the UPR pathway respectively.

In one embodiment, the signalization pathway is the CWI pathway. The CWI pathway (wherein CWI stands for Cell Wall Integrity) is a signalization pathway involved in the strengthening of the cell wall, and in the repair of damages of the cell wall, in conditions of environmental stress. Proteins of the CWI pathway include, but are not limited to, the Serine/Threonine kinase Pkc1 (Protein Kinase C 1); proteins of a cascade of MAP kinases (Mitogen activated protein kinases): Bck1 (Bypass of C Kinase), Mkk1 (Mitogen-activated protein Kinase-Kinase 1), Mkk2 (Mitogen-activated protein Kinase-Kinase 2), Slt2 (Suppression at Low Temperature 2); and the transcription factor Rlm1

(Resistance to Lethality of MKK1P386 overexpression 1), or homologs of these proteins in filamentous fungi.

In one embodiment, the activation of the CWI pathway may be determined through the analysis of the phosphorylation status of the proteins Bck1, Mkk1, Mkk2 and/or Slt2, wherein the phosphorylation of said proteins is indicative of the activation of the CWI pathway. Another way to analyze the activation status of the CWI pathway is the analysis of the expression of a gene placed under the control of a promoter responsive to the Rlm1 transcription factor.

Names of genes and proteins herein presented correspond to the genes and proteins of *Saccharomyces cerevisiae*. The skilled artisan knows how to identify the corresponding genes or proteins in another species of fungus.

In one embodiment of the invention, the inhibitor of the CWI pathway is an inhibitor of the kinase Pkc1, Bkc1, Mkk1, Mkk2 and/or Slt2. In another embodiment, the inhibitor of the CWI pathway is an inhibitor of the transcription factor Rlm1. In another embodiment, the inhibitor of the CWI pathway is an inhibitor of the protein Rom1 and/or Rho1.

In a preferred embodiment, the inhibitor of the CWI pathway is an inhibitor of Pkc1. In one embodiment, said inhibitor is a specific inhibitor of PKC from fungus.

Methods for identifying Pkc1 inhibitors are well known of the skilled artisan. An example of such method includes, but is not limited to, measuring the kinase activity of (partially) purified Pkc1 in presence of increasing amounts of potential inhibitors. Useful kits for measurement of PKC activity may be selected among PepTag Assay (Promega), MESACUP PKA/PKC assay kit; Cyclex PKC superfamily kinase assay kit (MBL);

Protein kinase C assay kits (PANVERA); Z'-Lyte FRET based kinase assay (Invitrogen); Omnia assay kit (Invitrogen). Other examples of such a method are biological tests carried out in the model yeast *Saccharomyces cerevisiae* (Tests C and D).

Test C is based on the essential role of Pkc1 in fungal cells: if its essential function is inhibited, the growth of the fungal cells will be affected. Therefore, in Test C, two different strains of *S. cerevisiae* are cultured in the presence of the tested compound: the first one is a wild-type strain, whereas the second overexpresses the fungal Pkc1 gene. If the tested compound is an inhibitor of the fungal Pkc1 protein, the growth of the wild-type strain will be inhibited, whereas the induction of the overexpression of the heterologous fungal Pkc1 gene will restore, at least partially, the growth rate. Test C is carried out in Example 3.

Test D is based on the fact that the protein Pkc1 is implied in the CWI pathway. In a situation where the CWI pathway is impaired, growth of fungal cells is less affected by a high osmotic pressure. Consequently, in Test D, a *S. cerevisiae* strain is cultured in conditions of high osmotic pressure, in the presence or in absence of the tested compound. If said compound is a Pkc1 inhibitor, it will inhibit the growth of cells in normal osmotic pressure conditions, but not, or less, in high osmotic pressure conditions. Test D is carried out in Example 3.

Examples of inhibitors of Pkc1 include, but are not limited to chelerythrin, chelerythrin chloride, 3-(1H-indol-3-yl)-4-[2-(4-methylpiperazin-1-yl)quinazolin-4-yl]pyrrole-2,5-dione (AEB071), 13-HODE, AEB-071, Annexin V, Aprinocarsen, ARC, Bisindolylmaleimide GF 109203X, bisphosphonate, Bryostatin-1, BSP-A1/-A2, Butein, Calphostin C, Curcumin, Daphnetin, Dexamethasone, Enzastaurin, Erbstatin, G06976, H-7 Hispidin, Hypocrellin A, hypericin, LY333531, Midostaurin, MT477, N-myristyl-Lys-Arg-Thr-Leu-Arg, NPC 15437, PAP, PKC412, R8605, RK-286C, Ro 31-8220, Rottlerin, ruboxistaurin, Sotrastaurin, Staurosporine, UCN-01, UCN-02, Vanicosides A and B, and Verbascoside.

Examples of PKC inhibitors also include, but are not limited to, compounds of general formula I, II or III as hereinabove described, and specifically compounds 1 to 4, chelerythrin, sanguinarin, berberin and coptisin.

In one embodiment, the signalization pathway is the HOG pathway. The HOG pathway (wherein HOG stands for High Osmolarity Glycerol) is a signalization pathway involved in the cellular response to an elevation in external osmolarity and potentially in cell wall biogenesis. Proteins of the HOG pathway include, but are not limited to, Ypd1 (tyrosine (Y) Phosphatase Dependent), Ssk1, Ssk2 and Ssk22 (Suppressor of Sensor Kinase 1, 2 and 22), Cdc42 (Cell Division Ring 42), Ste11, Ste 20 and Ste50 (STErile 11, 22 and 50), Pbs2 (Polymyxin B Sensitivity 2) and Hog1 (High Osmolarity Glycerol response 1), or homologs of these proteins in filamentous fungi.

In one embodiment, the activation of the HOG pathway may be determined through the analysis of the phosphorylation status of the proteins Ypd1, Ssk1, Ssk2, Ssk22, Cdc42, Ste11, Ste 20, Ste50, Pbs2 and/or Hog1.

In one embodiment of the invention, the inhibitor of the HOG pathway is an inhibitor of the protein Ypd1, Ssk1, Ssk2, Ssk22, Cdc42, Ste11, Ste 20, Ste50, Pbs2 and/or Hog1.

In one embodiment, the signalization pathway is the UPR pathway. The UPR pathway (wherein UPR stands for Unfolded Protein Response) is a stress signalization pathway involved in the cellular development and environmental adaptation in fungi. This pathway is more particularly involved in maintaining the Endoplasmic Reticulum homeostasis. Proteins of the UPR pathway include, but are not limited to, the serine-threonine kinase and endoribonuclease Ire1 (Inositol REquiring 1), the transcription factor Hac1, and homologs of these proteins in filamentous fungi.

In one embodiment, the activation of the UPR pathway may be determined through the analysis of the splicing of the hacA transcripts and the transcriptional induction of well-known UPR target genes, such as the chaperone Kar2 and the protein disulfide isomerase Pdi1.

In one embodiment of the invention, the inhibitor of the UPR pathway is an inhibitor of the serine-threonine kinase and endoribonuclease Ire1 and/or the transcription factor Hac1.

In one embodiment, the non-fungicidal amount of the potentiating agent is an amount of the potentiating agent (acting as a pathway inhibitor) wherein said agent does not have any fungistatic effect when fungi are cultured in the presence of said potentiating agent during 5 hours, preferably 10 hours, more preferably 20, 30 hours or more.

In another embodiment, the non-fungicidal amount of the potentiating agent is an amount of the agent wherein said product has a fungistatic effect but inhibits the growth of fungi by less than 20% as compared to control fungi cultured without the potentiating agent, when fungi are cultured in the presence of said potentiating agent during 5 hours, preferably 10 hours, more preferably 20, 30 hours or more.

Methods for determining non-fungicidal amount or concentration of a compound are well known from the skilled artisan. Examples of such methods include, but are not limited to, growth test in presence of increasing concentrations of said compound, which may be carried out in liquid or solid medium.

In one embodiment, the non-fungicidal amount of the at least one compound (potentiating agent) of the invention is determined in vitro by comparing the growth of the phytopathogenic fungal strain cultures in contact with increasing concentrations of said at least one potentiating agent, with the growth of a control culture of the phytopathogenic fungal strain, in the absence of said at least one potentiating agent; the last concentration of the increasing concentrations of the at least one potentiating agent resulting in substantially the same fungal culture growth as the control culture being retained as the non-fungicidal concentration of said at least one potentiating agent. In one embodiment, substantially refers to a 10% more or less pronounced fungal culture growth compared to the control culture growth. In one embodiment, substantially refers to a 20% more or less pronounced fungal culture growth compared to the control culture growth.

Preferably, the non-fungicidal amount of the potentiating agent is determined according to Test A as hereinabove described.

In one embodiment, the non-fungicidal amount of the potentiating agent (acting as a pathway inhibitor) ranges from about 1 nM to about 25 μM or from about 1 nM to about 15.

In one embodiment, the non-fungicidal amount of the potentiating agent (acting as a pathway inhibitor) ranges from about 1 to about 100 μM, preferably from about 1 to about 25 μM, more preferably from about 1 to about 15 μM or from about 1 to about 10 μM.

In one embodiment of the invention, the potentiating agent of a plant defense molecule is chelerythrin. In an embodiment, the non-fungicidal amount of the potentiating agent of a plant defense molecule, preferably chelerythrin, is below 50 μg/ml, preferably ranging from 1 μg/ml to less than 40 μg/ml, more preferably ranging from 5 μg/ml to 10 μg/ml.

However, one skilled in the art can understand that such non-fungicidal amount may need to be adapted when applied on field conditions. Indeed, in order to attenuate bioavailability obstacles such as plant organ permeability regarding the potentiating agent, the amount of the at least one potentiating agent may be adapted from about 1% to about 25%, or from about 5% to about 20% relative to the in-vitro determined non-fungicidal amount.

In one embodiment, said pathogenic fungus is selected from the group comprising *Alternaria brassicicola, Alternatria dauci* and *Venturia inaequalis.*

In one embodiment, the phytopathogenic fungi are pathogens of plants belonging to the clade of Angiosperms, preferably to the clade of Eudicots, more preferably to the clade of Rosids, even more preferably to the order of Brassicales and even more preferably to the family of Brassicacae, also referred as Crucifers family. Examples of plants from the Brassicacae family include, but are not limited to, *Brassica carinata, Brassica juncea, Brassica oleracea, Brassica napus, Brassica nigra* and *Brassica rapa.*

In one embodiment of the invention, the phytopathogenic fungi are pathogens of plants selected from the list comprising plants of the Brassicacae family, such as, for example, *Brassica oleracea*; plants of the Apiaceae family, such as, for example, *Daucus carota* subsp. *Sativus*; plants of the Vitaceae family, such as, for example, *Vitis vinifera*; or plants of the Rosaceae family, such as, for example, *Malus domestica.*

Examples of phytopathogenic fungi for specific plants are given in Table 1.

TABLE 1

| Plant | Phytopathogenic fungi |
|---|---|
| *Brassica oleracea* | *Alternaria brassicicola* |
| *Daucus carota* subsp. *Sativus* | *Alternaria dauci* |
| *Vitis vinifera* | *Botrytis cinerea* |
| *Malus domestica* | *Venturia inaequalis* |

In one embodiment, the plant defense molecule is a phytoalexin. Examples of phytoalexins include, but are not limited to, brassinin, camalexin, resveratrol, 3,5-dihydroxybiphenyl, aucuparin and 6-methoxymellein. In one embodiment, phytoalexins bear an indole scaffold such as brassinin or camalexin. In one embodiment, phytoalexins bear an phenolic scaffold such as 6-methoxymellein, resveratrol or the Rosaceae family phytoalexins, namely the apple-tree phytoalexins 3,5-dihydroxybiphenyl, aucuparin, methoxylation analogs thereof (3-hydroxy-5-methoxy-biphenyl, noraucuparin, 3,4,5-trihydroxybiphenyl, isoaucuparin, 2'-hydroxy-aucuparin, 2'-glucosyloxy-aucuparin, 2'-methoxy-aucuparin, rhaphiolepsin, or cyclizated derivatives thereof (2-hydroxy-4-methoxy-dibenzofuran, noreriobofuran, eriobofuran, hydroxy and methoxy analogs thereof).

In one embodiment, the phytoalexin is a phytoalexin synthesized by a plant belonging to the clade of Angiosperms, preferably to the clade of Eudicots, more preferably to the clade of Rosids, even more preferably to the order of Brassicales and even more preferably to the family of Brassicacae, also referred as Crucifers family Examples of plants from the Brassicacae family include, but are not limited to, *Brassica carinata, Brassica juncea, Brassica oleracea, Brassica napus, Brassica nigra* and *Brassica rapa.*

In one embodiment of the invention, the phytoalexin is a phytoalexin synthesized by a plant selected from the list comprising plants of the Brassicacae family, such as, for example, *Brassica oleracea*; plants of the Apiaceae family, such as, for example, *Daucus carota* subsp. *Sativus*; plants of the Vitaceae family, such as, for example, *Vitis vinifera*; or plants of the Rosaceae family, such as, for example, *Malus domestica.*

According to an embodiment, the exposure to a plant defense molecule may be a natural or an artificial exposure. As used herein, a "natural exposure" refers to an exposure during infection, in planta. Under natural exposure, an accumulation of plant defense molecule may occur as a result of the fungal infection, or as a result of other stimuli triggering the defense system of the plant organ. On the contrary, an "artificial exposure" refers to a provoked exposure to the molecule, for example in a culture medium or by application of said plant defense molecule on a fungus or on a culture of fungus.

Examples of plant defense molecules synthesized by selected plants are shown in Table 2.

TABLE 2

| Plant | Plant defense molecule |
|---|---|
| *Arabidopsis thaliana* | camalexin |
| *Brassica oleracea* | Brassinin |
| *Daucus carota* subsp. *Sativus* | 6-methoxymellein |
| *Vitis vinifera* | Resveratrol |
| *Malus domestica* | 3,5-dihydroxybiphenyl |

In one embodiment, the activation of a signalization pathway is determined after natural exposure to the molecule, for example by harvesting fungus from an infected plant. A non-limiting example of a method for determining the activation of a signalization pathway after natural exposure to the molecule is inoculating plant organs with said fungus, harvesting infected plant tissues comprising the phytopathogenic fungus, and extracting either proteins (for determining the activation of the CWI and/or HOG pathway(s)) or RNAs (for determining the activation of the UPR pathway) for analysis of the phosphorylation profile or of the expression profile, respectively.

In another embodiment, the activation of a signalization pathway is determined after artificial exposure to the molecule, for example by adding the molecule to the culture medium of a cultivated fungus, and harvesting exposed fungus. A non-limiting example of a method for determining the activation of a signalization pathway after artificial exposure to the molecule comprises adding said molecule to the culture medium of a cultivated fungus, harvesting the fungus, and extracting either proteins (for determining the activation of the CWI and/or HOG pathway(s)) or RNAs (for determining the activation of the UPR pathway) for analysis of the phosphorylation profile or of the expression profile, respectively.

In one embodiment of the invention, the plant defense molecule activating the signalization pathway is synthesized by the plant organ to be protected by the composition of the invention, said synthesis being either preexistent to infection or triggered by the infection.

In one embodiment, the composition of the invention further comprises a plant defense molecule. Such plant defense molecule may be incorporated in the composition of the invention in a purified form. Alternatively, the composition of the invention further comprises a plant defense molecule in the form of a plant extract such as for example a grapevine bark extract.

Advantageously, the composition of the invention comprises a plant defense molecule and a potentiating agent of said plant defense molecule.

In one embodiment of the invention, said plant defense molecule is present in the composition in a non-fungicidal amount.

In one embodiment, the non-fungicidal amount of the plant defense molecule is determined as the non-fungicidal amount of the potentiating agent.

In one embodiment, the non-fungicidal amount of the plant defense molecule is an amount of the plant defense molecule wherein said molecule does not have any fungistatic effect when fungi are cultured in the presence of said potentiating agent during 5 hours, preferably 10 hours, more preferably 20, 30 hours or more. In another embodiment, the non-fungicidal amount of the plant defense molecule is an amount of the plant defense molecule wherein said product has a fungicidal effect but inhibits the growth of fungi by less than 20% as compared to control fungi cultured without the plant defense molecule, when fungi are cultured in the presence of said potentiating agent during 5 hours, preferably 10 hours, more preferably 20, 30 hours or more.

Methods for determining non-fungicidal amount of a plant defense molecule are well known from the skilled artisan. Examples of such methods include, but are not limited to, growth test in presence of increasing concentrations of said compounds, which may be carried out in liquid or solid medium. Preferably, the non-fungicidal amount of a plant defense molecule is determined according to Test A as hereinabove described.

In one embodiment, the plant defense molecule is a phytoalexin as previously described.

In one embodiment of the invention, the plant defense molecule present in the composition is the same than the plant defense molecule synthesized by the plant organ to be protected by the composition of the invention. Preferably, according to this embodiment, the potentiating agent of a plant defense molecule is a homologous potentiating agent.

In another embodiment of the invention, the plant defense molecule present in the composition is different from the plant defense molecule synthesized by the plant organ to be protected by the composition of the invention. According to this embodiment, the potentiating agent of a plant defense molecule may be a homologous or a heterologous potentiating agent of a plant defense molecule.

The present invention also relates to a product comprising a potentiating agent of a plant defense molecule, in combination with a plant defense molecule.

In one embodiment, said product comprises a non-fungicidal dose of said potentiating agent. In one embodiment, said product comprises a non-fungicidal dose of said plant defense molecule. In one embodiment, said product comprises a non-fungicidal dose of said potentiating agent and a non-fungicidal dose of said plant defense molecule.

In one embodiment, the composition or the product of the invention further comprises an agent for stimulating the production of a plant defense molecule such as, for example, phytoalexin, by a plant organ; an insecticide and/or a herbicide.

In one embodiment, said agent for stimulating the production of a plant defense molecule is present in the composition in a non-fungicidal amount. Preferably, said non-fungicidal amount is determined as previously detailed for the case of the potentiating agent. In one embodiment, the non-fungicidal amount of the agent for stimulating the production of a plant defense molecule is determined according to Test A.

In one embodiment, the agent for stimulating the production of a plant defense molecule is selected from acibenzolar-S-methyl (such as for example BION 50 WG® or DACONIL ACTION®), chitosan (such as for example BIOREND®), laminarin (such as for example VACCIPLANT®), a plant extract such as *Reynoutria sachalinensis* extract (such as for example REGALIA®), calcium prohexadione (such as for example APOGEE® or REGALIS®), harpine (such as for example PROACT®), yeast wall extracts such as cerevisane (such as for example ROMEO®), oligogalacturonides, oligogalacturonides in association with chitosan (such as for example MESSAGER® or GALOPIN+®) and calcium phosphite (such as for example SDN TOP® or SORIALE®).

The present invention also relates to a product comprising a potentiating agent of a plant defense molecule, in combination with an agent for stimulating the production of a plant defense molecule by a plant organ; an insecticide and/or a herbicide.

In an embodiment, the composition or the product of the invention does not comprise a fungicide in a fungicidal amount.

In one embodiment of the invention, the composition or the product of the invention consists of a combination of a homologous potentiating agent of a plant defense molecule and an agent for stimulating the production of said plant defense molecule by the plant organ to be protected or treated.

The present invention also relates to a phytosanitary or phytopharmaceutical product comprising a composition or a product as herein above described.

Accordingly, the present invention also relates to a phytosanitary or phytopharmaceutical product comprising a potentiating agent of a plant defense molecule, and optionally a plant defense molecule and/or an agent for stimulating the production of a plant defense molecule by a plant organ, an insecticide and/or a herbicide.

The present invention also relates to a composition comprising a phytosanitary or phytopharmaceutical product as herein above described in association with at least one phytopharmaceutical vehicle.

In one embodiment, the composition or the product of the invention is in a solid form, such as, for example, granules, wettable powders, water dispersable granules or powders and the like.

In another embodiment, the composition or the product of the invention is in a liquid form, such as, for example, a suspension, a solution or an emulsion, such as, for example, an oil-in-water emulsion or a water-in-oil emulsion.

In one embodiment, the composition or the product of the invention may be formulated as a concentrate to be diluted, such as, for example, a soluble concentrate, an emulsifiable concentrate, and the like.

In one embodiment, the composition or the product of the invention may comprise additional agents, such as, for example, natural or regenerated mineral substances, solvents, dispersants, solid carriers, surfactants, wetting agents, tackifiers, thickeners, or binders.

Examples of solvents include, but are not limited to, aromatic hydrocarbons, such as, for example, xylene mixtures or substituted naphthalenes; phthalates, such as, for example, dibutyl phthalate or dioctyl phthalate; aliphatic hydrocarbons, such as, for example, cyclohexane or paraffins; alcohols and glycols and their ethers and esters, such as, for example, ethanol, ethylene glycol, ethylene glycol monomethyl or monoethyl ether; ketones, such as, for example, cyclohexanone; strongly polar solvents, such as, for example, N-methyl-2-pyrrolidone, dimethyl sulfoxide or dimethylformamide; vegetable oils or epoxidised vegetable oils, such as, for example, epoxidised coconut oil or soybean oil; and water.

Examples of solid carriers include, but are not limited to, natural mineral fillers, such as, for example, calcite, talcum, kaolin, montmorillonite or attapulgite; highly dispersed silicic acid or highly dispersed absorbent polymers; pumice, broken brick, sepiolite or bentonite; calcite or sand; dolomite or pulverized plant residues.

Examples of surfactants include, but are not limited to, anionic surfactants including; alkylsulfosuccinic acid salts, condensated phosphate acid salts, alkylbenzenesulfonic acid salts such as, for example, dodecylbenzenesulfonic acid sodium salt, alkylnaphthalenesulfonic acid salts, formalin condensates of naphthalenesulfonic acid salts, ligninsulfonic acid salts, polycarboxylic acid salts, alkylethersulfuric acid salts, polyoxyethylene-alkylarylphenylether-sulfuric acid salts, polyoxyethylene-alkylarylether-sulfuric acid salts, polyoxyethylene-alkylaryl-sulfuric acid salts, polyoxyethylene-alkylaryether-sulfate ester salts, polyoxyethylene-alkylarylether-acetate ester-sulfuric acid salts; nonionic surfactants such as, for example, polyoxyethylene-alkylether, polyoxyethylene-alkylarylether, polyoxyethylene-alkylarylphenylether, polyoxyethylene-styrylphenylether, polyoxyethylene-alkyl ester, sorbitan-alkyl-ester, polyoxyethylene-sorbitanalkyl-ester, and polyoxyethylene-polyoxypropyleneglycol. As used herein, the salt form includes alkali-metal salts, ammonium salts, and amine salts.

The present invention also relates to a coating, dressing or pelleting composition comprising or consisting of a composition or a product as herein above described.

The present invention also relates to a composition comprising or consisting of a composition or a product as herein above described for use for coating, dressing or pelleting a plant organ, preferably a seed.

The present invention also relates to the use of a composition or of a product as herein above described for coating, dressing or pelleting a plant organ, preferably a seed.

The present invention also relates to a coated, dressed or pelleted plant organ, preferably a coated, dressed or pelleted seed, wherein said coating, dressing or pelleting comprises or consists of or consists essentially of a composition or a product according to the invention.

In one embodiment, the coating, dressing or pelleting composition comprises or consists of or consists essentially of a potentiating agent of a plant defense molecule combined with said plant defense molecule. In one embodiment, the coated, dressed or pelleted plant organ, preferably seed, is coated, dressed or pelleted with a composition comprising or consisting of or consisting essentially of a potentiating agent of a plant defense molecule combined with said plant defense molecule.

The present invention also relates to a method for preventing, controlling or treating a fungal infection on a plant organ comprising applying on said plant organ the product or the composition according to the invention. Preferably, a phytopharmaceutically effective amount of said product or of said composition is applied on the plant organ.

The present invention also relates to a composition or product as herein above described for, or for use in, preventing, controlling or treating a fungal infection on a plant organ, wherein said composition or product, preferably a phytopharmaceutically effective amount of said composition or product, is applied on said plant organ.

The present invention also relates to the use of a composition or product as herein above described for preventing, controlling or treating a fungal infection on a plant organ, wherein said composition or product, preferably a phytopharmaceutically effective amount of said composition or product, is applied on said plant organ.

The present invention also relates to a method for preventing, controlling or treating a fungal infection on a plant organ comprising applying to said plant organ a non-fungicidal amount or a potentiating amount of a composition comprising a potentiating agent of a plant defense molecule, in association with a phytopharmaceutical vehicle.

The present invention also relates to a method for preventing, controlling or treating damages caused by a fungal infection on a plant organ comprising applying on said plant organ the composition or product according to the invention. Preferably, a phytopharmaceutically effective amount of said composition or product of the invention is applied on the plant organ.

Examples of damages caused by a fungal infection on a plant organ include, but are not limited to, necrosis, wilting, rot, damping off and the like.

The present invention also relates to a composition or product as herein above described for, or for use in, preventing, controlling or treating damages caused by a fungal infection on a plant organ, wherein said composition or product, preferably a phytopharmaceutically effective amount of said composition or product, is applied on said plant organ.

The present invention also relates to the use of a composition or product as herein above described for preventing, controlling or treating damages caused by a fungal infection on a plant organ, wherein said composition or product, preferably a phytopharmaceutically effective amount of said composition or product, is applied on said plant organ.

The present invention also relates to a method for improving the growing characteristics of a plant organ comprising applying on said plant organ the composition or product according to the invention.

Without willing to be bound to a theory, the inventors suggest that by preventing, controlling and/or treating fungal infections, the composition or product of the invention allows a decrease of the part of the metabolism of the plant dedicated to the fight against said fungal infections.

The present invention also relates to a composition or product as herein above described for, or for use in, improving the growing characteristics of a plant organ, wherein said composition or product, preferably a phytopharmaceutically effective amount of said composition or product, is applied on said plant organ.

The present invention also relates to the use of a composition or product as herein above described for improving the growing characteristics of a plant organ, wherein said composition or product, preferably a phytopharmaceutically effective amount of said composition or product, is applied on said plant organ.

In one embodiment, in the methods of the invention as herein above described, the application of the product or composition of the invention on said plant organ is carried out by foliar application, drench, spraying, atomizing, dusting, scattering, coating or pouring.

In one embodiment of the invention, the potentiating agent of a plant defense molecule is present in the composition in a potentiating amount. In one embodiment, the methods of the invention as herein above described comprise the application of a potentiating amount of the potentiating agent on said plant organ.

Methods for determining potentiating amount of the potentiating agent are well known from the skilled artisan. Examples of such methods include, but are not limited to, growth test in presence of increasing concentrations of said compounds, which may be carried out in liquid or solid medium. Preferably, the potentiating amount of the potentiating agent is determined according to Test B as hereinabove described.

The compositions and products of the invention present the following advantages:

In one embodiment, the product or composition of the invention allows a decrease of the quantity of fungicides to be used to fight against a fungal infection, as non-fungicidal amounts of potentiating agents of plant defense molecules, of plant defense molecules, of insecticide, of herbicide and of agents for stimulating the synthesis of a plant defense molecule are present in the product or composition of the invention.

In one embodiment, the product or composition of the invention may be used for fungi destruction in situ, i.e. when said fungi are attacking a plant organ of interest. Said embodiment applied, for example, when the potentiating agent is a homologous potentiating agent. The product or the composition of the invention is thus selective of fungi attacking a plant organ of interest.

In another embodiment, the product or composition of the invention is fungicide whatever the situation, i.e. when fungi are attacking a plant organ or not. Said embodiment applied, for example, when the product or the composition of the invention comprises a plant defense molecule and a potentiating agent of said plant defense molecule.

In one embodiment, the product or composition may be adapted to a particular situation of attack of a particular plant organ by a particular fungus. According to this embodiment, the inhibitor may be specific from said particular fungus. Still according to this embodiment, the plant defense molecule, or the agent for stimulating the production of a plant defense molecule may be specific of the attacked plant organ.

Therefore, in an alternative perspective, the method of the invention is a method for enhancing the efficacy of an antifungal treatment, said method comprising applying on the plant organ infected by a phytopathogenic fungus, a composition comprising:
 a phytotherapeutically effective amount of an antifungal agent,
 at least one potentiating agent in a concentration equal or inferior to the determined non-fungicidal concentration, as previously described, and
 a phytopharmaceutical vehicle.

In one embodiment, enhancing the efficacy of an antifungal treatment refers to a reduced incidence of the phytopathogen infection. According to such embodiment, applying the composition of the invention leads to a decrease of at least about 5%, or at least about 10% in the number/percentage of infected plant organs in the plant culture treated with the method of the invention, compared to the number/percentage of infected plant organs in a plant culture treated with the phytotherapeutically effective amount of the antifungal agent alone.

In one embodiment, enhancing the efficacy of an antifungal treatment refers to a reduced severity of the phytopathogen infection. According to such embodiment, applying the composition of the invention leads to a decrease of at least about 5%, or at least about 10% of the percentage of infected plant organs' surface in the plant culture treated with the method of the invention, compared to the percentage of infected plant organs' surface of infected plant organs in a plant culture treated with the phytotherapeutically effective amount of the antifungal agent alone.

Surprisingly, by supplementing an antifungal treatment with a substantially non-fungicidal amount of a potentiating agent according to the invention, leads to a substantial improvement of the phytopathogenic infection prevention, control or treatment.

According to a last aspect, the invention relates to a method for reducing the amount of an antifungal agent while maintaining or increasing the efficacy of the prevention, control or treatment of a phytopathogenic infection onto a plant organ. Such method comprises applying on the plant organ a composition comprising:
 a phytopharmaceutically sub-effective amount of said antifungal agent in association with:
 a phytopharmaceutical vehicle, and
 at least one potentiating agent as previously described in a concentration substantially equal or inferior to its non-fungicidal concentration.

One skilled in the art knows the phytopharmaceutically effective amount of one antifungal agent which is often established by regulatory provisions. In one embodiment, phytopharmaceutically sub-effective amount of the antifungal agent is at least 2%, at least 5%, at least 8%, at least 10%, at least 12%, at least 15%, at least 18%, at least 20%, at least 22%, at least 25%, at least 28%, or at least 30% inferior to the phytopharmaceutically effective amount of the antifungal agent.

In one embodiment, the sub-effective concentration of the antifungal agent is determined by comparing:
i) the incidence or the severity of the phytopathogenic fungal infection on a plant culture in contact with increasing concentrations of said at antifungal agent, with
ii) the incidence or the severity of the phytopathogenic fungal infection on a control plant culture of the phytopathogenic fungal strain, in the absence of said at least one potentiating agent (i.e. with the phytopharmaceutical vehicle only such as for example water);

the last concentration of the increasing concentrations of the antifungal agent resulting in substantially the same incidence or severity of the phytopathogenic fungal infection as the control culture being retained as the sub-effective concentration of said at least one potentiating agent.

In the context of this aspect of the invention, "substantially the same incidence of the phytopathogenic fungal infection as the control culture" should be understood as more or less about 20%, or more or less about 10% the number/percentage of infected plant organs in the assessed plant culture treated with the sub-effective concentration of the anti-fungal agent, compared to the number/percentage of infected plant organs in the control plant culture.

Likewise, "substantially the same severity of the phytopathogenic fungal infection as the control culture" should be understood as more or less about 20%, or more or less about 10% the percentage of infected plant organs' surface in the assessed plant culture treated with the sub-effective concentration of the anti-fungal agent, compared to the percentage of infected plant organs' surface in the control plant culture.

In one embodiment, the sub-effective concentration of the antifungal agent is determined as the non-fungicide concentration of the potentiating agent described above.

"maintaining the efficacy of the prevention, control or treatment of a phytopathogenic infection" refers to a more or less 2% of the incidence or severity relative to a prevention, control or treatment by application of a phytopharmaceutically effective amount of the antifungal agent alone or eventually in association with a phytopharmaceutically acceptable vehicle.

"increasing the efficacy of the prevention, control or treatment of a phytopathogenic infection" refers to an at least 3%, at least 4%, at least 5%, at least 8%, at least 10%, at least 12%, at least 15%, at least 18% or at least 20% decrease of the incidence or severity of the phytopathogenic infection relative to a prevention, control or treatment by application of a phytopharmaceutically effective amount of the antifungal agent alone or eventually in association with a phytopharmaceutically acceptable vehicle.

In one embodiment, the antifungal agent is acibenzolar-S-methyl and the phytopharmaceutically sub-effective concentration thereof ranges from about 10 ppm to about 500 ppm, from about 50 ppm to about 450 ppm, from about 50 ppm to about 400 ppm, from about 100 ppm to about 375 ppm or from about 200 ppm to about 400 ppm.

In one embodiment, the antifungal agent is chitosan and the phytopharmaceutically sub-effective concentration thereof ranges from about 500 ppm to about 5000 ppm, from about 600 ppm to about 4500 ppm, from about 800 ppm to about 4000 ppm, from about 1000 ppm to about 5000 ppm or from about 2000 ppm to about 4000 ppm.

As previously discussed, the in-vitro defined non-fungicidal amount may need to be adapted when applied on field conditions, namely in order to attenuate bioavailability obstacles such as plant organ permeability regarding the potentiating agent. Thus, the amount of the at least one potentiating agent may be considered from about ±1% to about ±38%, from about ±5% to about ±38%, from about ±10% to about ±30%, from about ±10% to about ±25%, from about ±10% to about ±20% relative to the in-vitro determined non-fungicidal amount. It is to be noted, that such in vitro determined non-fungicidal amount, does not exert any significant effects on the phytopathogenic fungus infection incidence or severity.

In one embodiment, a concentration substantially equal or inferior to its non-fungicidal concentration of the at least one potentiating agent is from 1 nM to 40 µM, from 5 nM to 40 µM, from 1 µM to 40 µM, from 1 µM to 38 µM, from 1 µM to 25 µM, from 1 µM to 20 µM, from 1 µM to 15 µM, from 1 µM to 10 µM, from 1 µM to 5 µM.

In one embodiment, the method for enhancing the efficacy of an antifungal treatment and or/the method for reducing the amount of an antifungal agent while maintaining or increasing the efficacy of the prevention, refer to any one of the phytopathogenic systems as herein above described.

Lastly, it should be pointed out the phytopharmaceutical compositions enabled in any one of the aspects of the method according to the present invention, is also within the scope of the present application.

EXAMPLES

The present invention is further illustrated by the following examples. In these examples, spectrometry was performed using the SPECTROstar nano device commercialized by BMG LABTECH.

Example 1: Determination of the Potentiating Amount of Chelerythrin a) In Vitro Determination of the Non Fungicidal Amount of Chelerythrin

*Alternaria brassicicola* strains were cultivated at 24° C. on potato dextrose (PD) medium (Cat. No. 213200; Becton Dickinson, USA).

For inoculum preparation, conidia were collected from 8-days-old solid cultures by adding PD broth followed by gentle scraping of the agar plates. They were counted in a Thoma's chamber and the conidial suspensions were diluted to the concentration of $10^5$ conidia/mL.

Growth was automatically recorded for at least 30 hours at 25° C. using a nephelometric reader (NEPHELOstar Galaxy, BMG Labtech, Germany) equipped with a 635-nm laser as radiation source. During incubation, the 96-well plates were subjected to shaking at 175 rpm for 5 minutes every 10 minutes. Measurements were done every hour with a gain value of 90 and a percentage of the maximum value of 20%. Each well was measured for 0.1 second with a laser beam of 2.5 mm.

Figure 1:
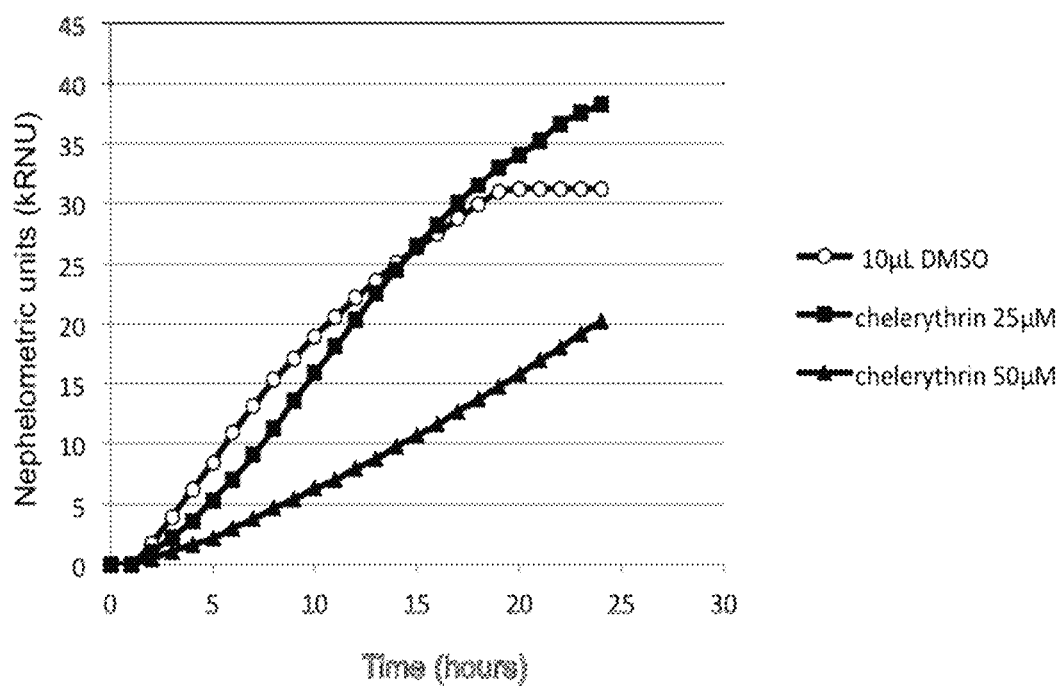
FIG. 1 is a growth curve describing the effect of increasing concentrations of chelerythrin on *Alternaria brassicicola*.

Chelerythrin (25 µM or 50 µM, test wells) or 10 µL of DMSO (chelerythrin solvent, control wells) were added on wells, and growth curves were drawn (FIG. 1).

As shown in FIG. 1, a concentration of 25 µM of chelerythrin does not inhibit *Alternaria brassicicola* growth. Said concentration thus corresponds to a non-fungicidal amount.

b) In Vitro Determination of the Non Fungicidal Amount of Camalexin

*Alternaria brassicicola* growth was measured as described in Example 1a.

Figure 2:
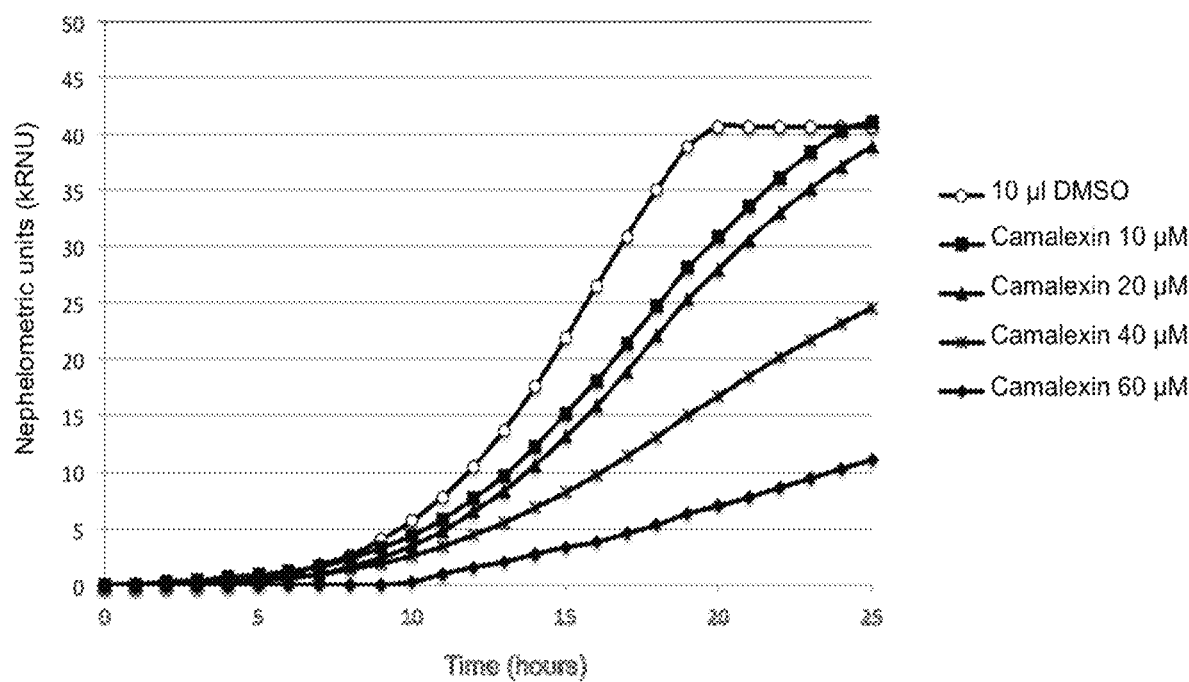
FIG. 2 is a growth curve describing the effect of increasing concentrations of camalexin on *Alternaria brassicicola*.

Camalexin (10, 20, 40 or 60 µM, test wells) or 10 µL of DMSO (chelerythrin solvent, control wells) were added on wells, and growth curves were drawn (FIG. 2).

As shown in FIG. 2, the concentrations of 10 and 20 µM of camalexin do not inhibit *Alternaria brassicicola* growth of more than 20%. Said concentrations thus correspond to non-fungicidal amounts.

c) In Vitro Determination of the Potentiating Amount of Chelerythrin

The potentiating effect of chelerythrin is measured in a suspension of conidia treated with a plant defense molecule, camalexin, which is present at a non-fungicidal amount as determined hereinabove. Said non-fungicidal amount is consistent with the amount of camalexin produced by an infected plant organ.

*Alternaria brassicicola* growth was measured as described hereinabove.

Figure 3:
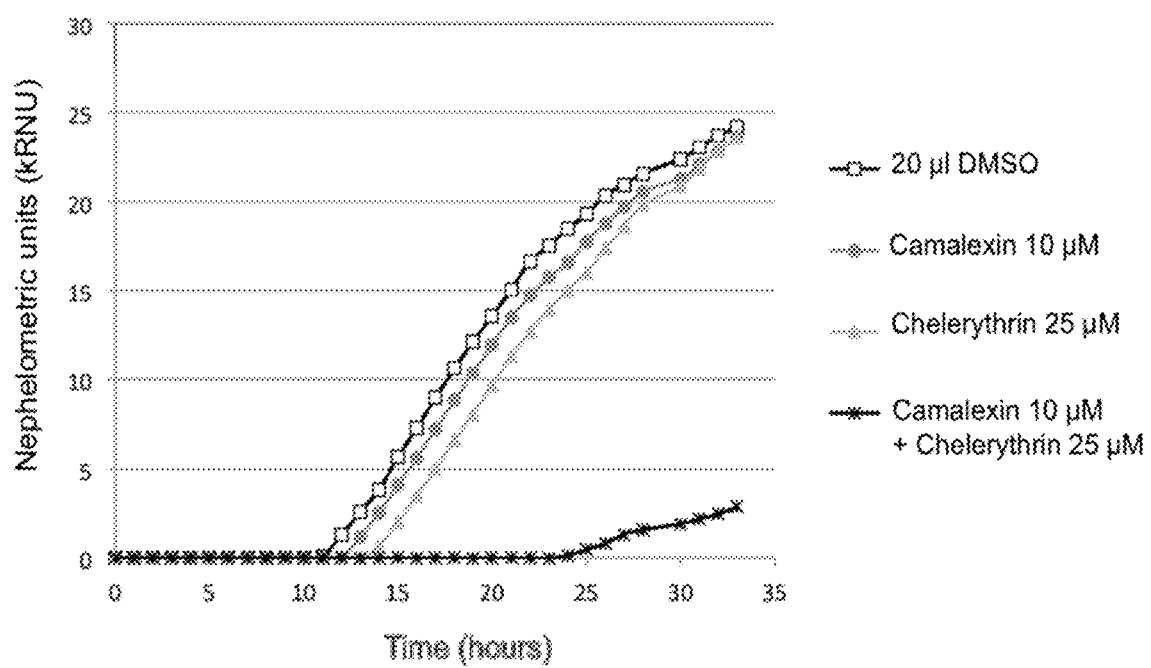
FIG. 3 is a growth curve showing the synergistic effect of 25 µM of chelerythrin and of 10 µM of camalexin on growth of *Alternaria brassicicola*.

A non-fungicidal amount of chelerythrin (as determined in Example 1a) and/or a non-fungicidal amount of camalexin (as determined in Example 1b) or 10 µL of DMSO are added per well, and growth curves were drawn (FIG. 3).

As shown in FIG. 3, a surprising synergistic effect, which is a potentiating effect, is shown on growth of *Alternaria brassicicola*. Indeed, the combination of a non-fungicidal amount of chelerythrin and of a non-fungicidal amount of camalexin leads to a drastic inhibition of *Alternaria brassicicola* growth. The concentration of 25 µM of chelerythrin is thus a potentiating amount.

Example 2: In Vivo Effect of the Composition of the Invention

Example 2 discloses a protocol for determining the in vivo efficacy of the composition of the invention, comprising a potentiating amount of chelerythrin (25 µM), as determined in Example 1.

5 µL drops of *Alternaria brassicicola* conidia suspension ($10^5$ to $10^3$ conidia/mL) were inoculated on intact or pre-wounded (i.e wherein the synthesis of plant defense molecules such as Brassinin was naturally triggered by the aggression) leaves of *B. oleracea* cv *Bartolo* plants at stages 4-6 leaves per plant. Inocula were deposited on the left and right sides symmetrically from the central vein: inocula comprising 25 µM of chelerythrin were deposited on the right side, and inocula comprising DMSO were deposited on the left side. The plants were then maintained under saturing humidity (100% relative humidity). Symptoms were observed at day 6 post-infection (6 dpi).

Figure 4:
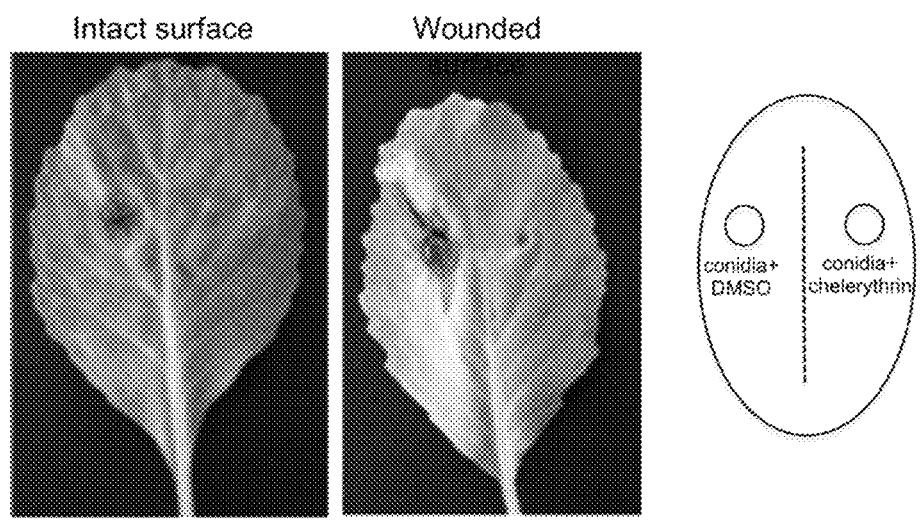
FIG. 4 is a combination of pictures of cabbage leaves (*Brassica oleracea* cv *Bartolo*) inoculated with *Alternaria brassicicola*, and treated with a control solution or with the composition of the invention, as stated in Panel C. (A) unwounded leaves. (B) wounded leaves.

As shown in FIG. 4, the composition of the invention limits in vivo the fungal infection of cabbage leafs.

Example 3: In Vivo Determination of the Inhibition of PKC by Chelerythrin

1—Test C of the Invention

Construction of a *S. cerevisiae* strain overexpressing *Alternaria brassicicola* Pkc1 The cDNA encoding the Pkc1 gene of *Alternaria brassicicola* (http://genome.jgi-psf.org/Altbr1/Altbr1.home.html; sequence ref: AB07449.1) was amplified by PCR and cloned into a pYES2-CT vector (Invitrogen, Paisley, UK). The resulting vector (pYES-PKC) was inserted in a BY4743 strain of *Saccharomyces cerevisiae*.

Growth Monitoring

Growth of this strain was monitored in an inducing medium (GS uracil-free medium supplemented with galactose) in presence of increasing concentrations of chelerythrin (0, 25, 50 or 75 µM), and was compared with the growth of a control strain (BY4743 strain transformed with the empty pYES2-CT vector). Growth was measured by spectrometry (Optic density: 600 nm). Inhibition of growth was assessed by comparison of the area under the curves.

Results are shown in Table 3 below.

TABLE 3

| Condition (concentration of chelerythrin) | Area under the curve | Inhibition |
|---|---|---|
| pYES2-CT | 15.1 | — |
| pYES2-CT (25 µM) | 8.6 | 43% |
| pYES2-CT (50 µM) | 3.2 | 79% |
| pYES2-CT (75 µM) | 2.5 | 84% |
| pYES2-PKC | 12.6 | — |
| pYES2-PKC (25 µM) | 10.7 | 15% |

TABLE 3-continued

| Condition (concentration of chelerythrin) | Area under the curve | Inhibition |
|---|---|---|
| pYES2-PKC 50 (50 μM) | 9.4 | 25% |
| pYES2-PKC 75 (75 μM) | 8.8 | 30% |

Chelerythrin inhibits the growth of strains expressing normal levels of Pkc1. The inhibition is less efficient in cells overexpressing Pkc1. Therefore, chelerythrin probably is an inhibitor of Pkc1.

2—Test D of the Invention

The growth of a BY4743 strain of *Saccharomyces cerevisiae* on a liquid SD medium comprising increasing concentrations of chelerythrin (0, 10, 15, 20 or 25 μM) was monitored and compared to the growth of the same strain on a liquid SD medium containing 1M of sorbitol (high osmotic pressure conditions) in presence of increasing concentrations of chelerythrin.

Growth was measured by spectrometry (optic density: 600 nm) Inhibition of growth was assessed by comparison of the area under the curves. Results are shown in the Table 4 below.

TABLE 4

| Medium | Concentration of chelerythrin (μM) | Area under the curve | Inhibition (%) |
|---|---|---|---|
| SD | 0 | 15.7 | — |
|  | 10 | 14.3 | 10 |
|  | 15 | 11.8 | 26 |
|  | 20 | 10.4 | 35 |
|  | 25 | 8.1 | 49 |
| SD + Sorbitol | 0 | 5.0 | — |
|  | 10 | 5.2 | −3 |
|  | 15 | 5.0 | 1 |
|  | 20 | 2.0 | 0 |

Chelerythrin inhibits the growth of a wild-type strain in normal osmotic pressure conditions, but not in high osmotic pressure conditions. This result seems to confirm the inhibitory action of chelerythrin on Pkc.

Example 4: Triads Compounds/Plant Defense Molecules/Phytopathogenic Fungus

In the Table 5 below are shown compounds (column 1) having a potentiating effect of a plant defense molecule (column 2) for the inhibition of a pathogenic fungus (column 3). The type of the potentiating agent in this particular situation is given in column 4 (homologous or heterologous). Triads were identified according to Test B.

TABLE 5

| Compound | Plant defense molecule | Phytopathogenic fungus | Type of potentiating agent |
|---|---|---|---|
| 1 | Resveratrol | *Alternaria brassicicola* | Heterologous |
| 2 | Brassinin | *Alternaria brassicicola* | Homologous |
|  | Brassinin | *Botrytis cinerea* | Homologous |
|  | Camalexin | *Botrytis cinerea* | Homologous |
|  | 6-methoxymellein | *Alternaria dauci* | Homologous |
| 3 | Resveratrol | *Alternaria brassicicola* | Heterologous |
| 4 | Brassinin | *Alternaria brassicicola* | Homologous |
|  | Resveratrol | *Alternaria brassicicola* | Heterologous |
| 5 | Brassinin | *Alternaria brassicicola* | Homologous |
|  | Resveratrol | *Alternaria brassicicola* | Heterologous |

TABLE 5-continued

| Compound | Plant defense molecule | Phytopathogenic fungus | Type of potentiating agent |
|---|---|---|---|
| Coptisin | Brassinin | *Alternaria brassicicola* | Homologous |
|  | Camalexin | *Alternaria brassicicola* | Homologous |
| Chelerythrin | Brassinin | *Alternaria brassicicola* | Homologous |
|  | Camalexin | *Alternaria brassicicola* | Homologous |

Example 5: Potentiating Effect of *Macleaya cordata* Crude Extract Against *Alternaria Dauci*

A crude extract of *Macleaya cordata* was analyzed phytochemical analysis, namely by means of HPLC-UV chromatography and $^1$H-NMR spectrometry using p-anisaldehyde as internal standard.

The HPLC-UV at 270 nm showed two major peaks corresponding to sanguinarine and chelerythrine having a retention time of 10.3 minutes and 12.45 minutes respectively.

The $^1$H-NMR spectrum confirmed that sanguinarine is the major alkaloid and indicated that the molar ratio of sanguinarine/chelerythrine is about 2.8 (based on the deshielded H-5 proton of the benzo[c]phenantridine scaffold at 10.14 ppm for the sanguinarine and 10.09 ppm for the chelerythrine).

The global phytochemical analysis showed that the *M. cordata* extract contains about 40% of sanguinarine, in weight relative to the total extract.

Figure 5:
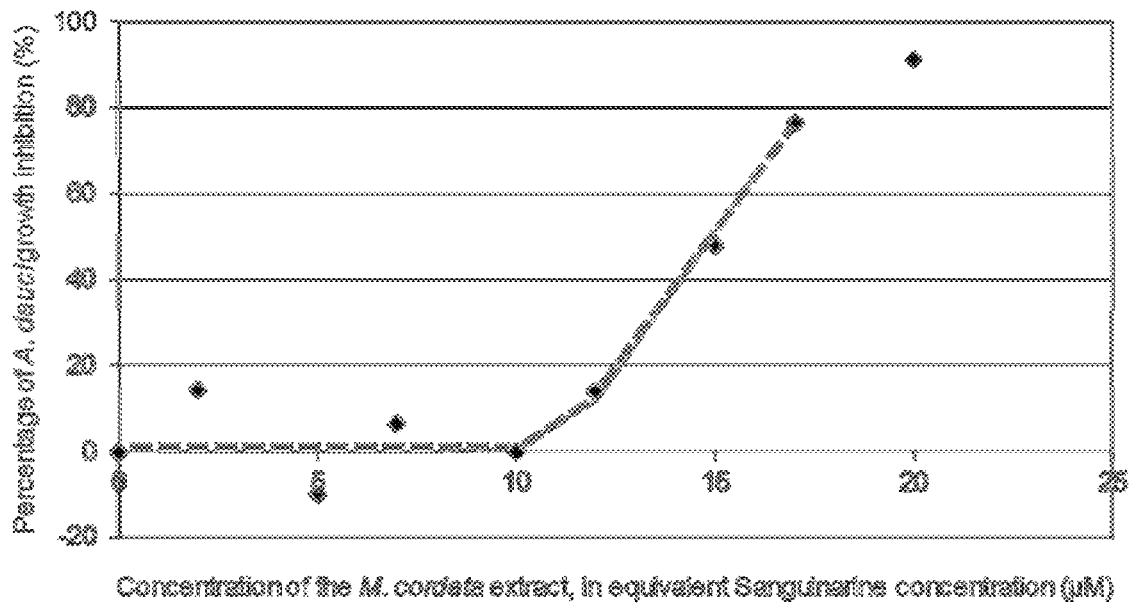
FIG. 5 is a growth curve describing the effect of increasing concentrations of *Macleaya cordata* extract on *Alternaria dauci*, showing the non-fungistatic concentration of 10 µM, expressed in the equivalent sanguinarine concentration.

The non-fungicidal amount of the sanguinarine contained in *M. cordata* extract against *A. dauci* strain was determined as 12 μM or 4 ppm according to the protocol described in Example 1. The results regarding the growth inhibition of *A. dauci* by *M. cordata* extract are presented in FIG. 5.

Thus, the non-fungicidal amount of *M. cordata* extract against *Alternaria dauci* is 10 ppm.

Following the aforementioned growth inhibition protocol, the following treatments are assessed:
- 6-methoxymellein 125 μM,
- 6-methoxymellein 100 μM,
- 6-methoxymellein 125 μM and *M. cordata* extract (10 μM of Sanguinarine),
- 6-methoxymellein 100 μM and *M. cordata* extract (10 μM of Sanguinarine).

Figure 6:
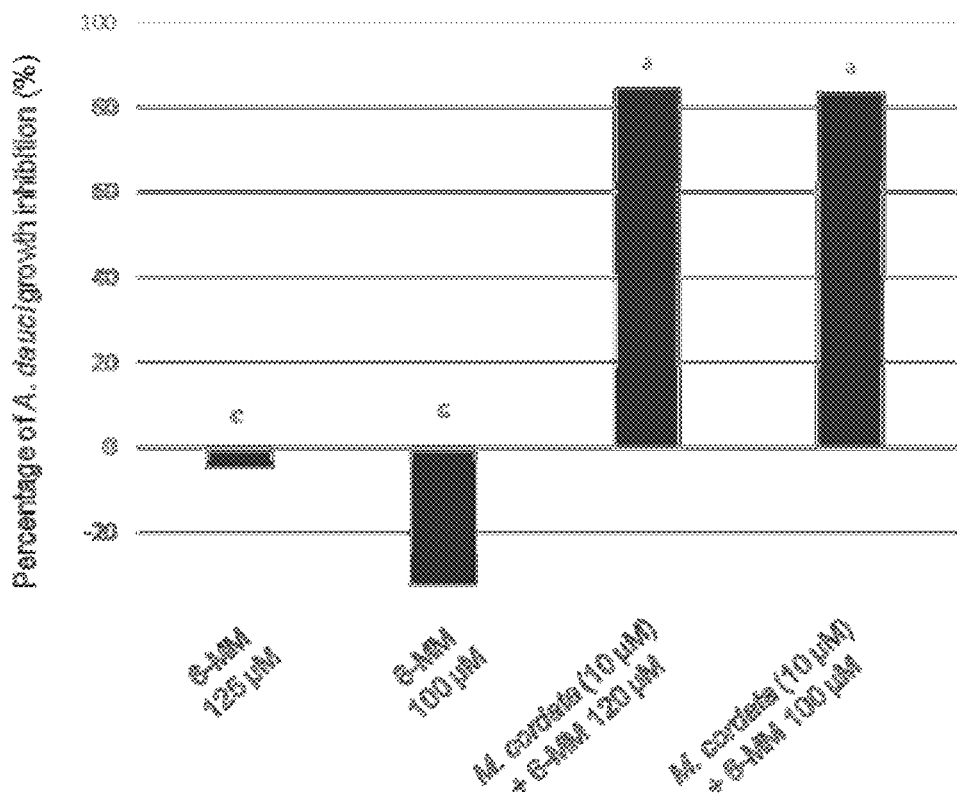
FIG. 6 is a graph showing the non-fungistatic effects of the carrot phytoalexin 6-methoxymellein (6-MM) at a concentration of 125 µM and 100 µM on the growth of *Alternaria dauci*. The graph further shows that the association of non-fungistatic concentrations of *Macleaya cordata* extract (10 µM, expressed in the equivalent sanguinarine concentration) and 6-methoxymellein (6-MM, at a concentration of 125 µM and 100 µM respectively) presents synergistic effect and effectively inhibits the growth of *Alternaria dauci*.

The results are illustrated in FIG. 6.

Interestingly, 6-methoxymellein, the phytoalexin of the *Daucus carotta* (carrot) plant species did not inhibit the growth of *Alternaria dauci* at the concentration of 100 or 125 μM.

Surprisingly, the association of non-fungicide amounts of 6-methoxymellein and M *cordata* extract showed a synergistic effect resulting in a significant fungal growth inhibition.

Example 6: In Vitro Non-Fungicidal Amount of *Macleaya cordata* Crude Extract Against *Venturia inaequalis*

The non-fungicidal amount of the sanguinarine contained in *M. cordata* extract against *Venturia inaequalis* 2557 09BC2014 strain was determined as 5 μM or 1.66 ppm according to the protocol described in Example 1.

Thus, the in vitro non-fungicidal amount of *M. cordata* extract against *Venturia inaequalis* is 4.15 ppm.

Figure 7:
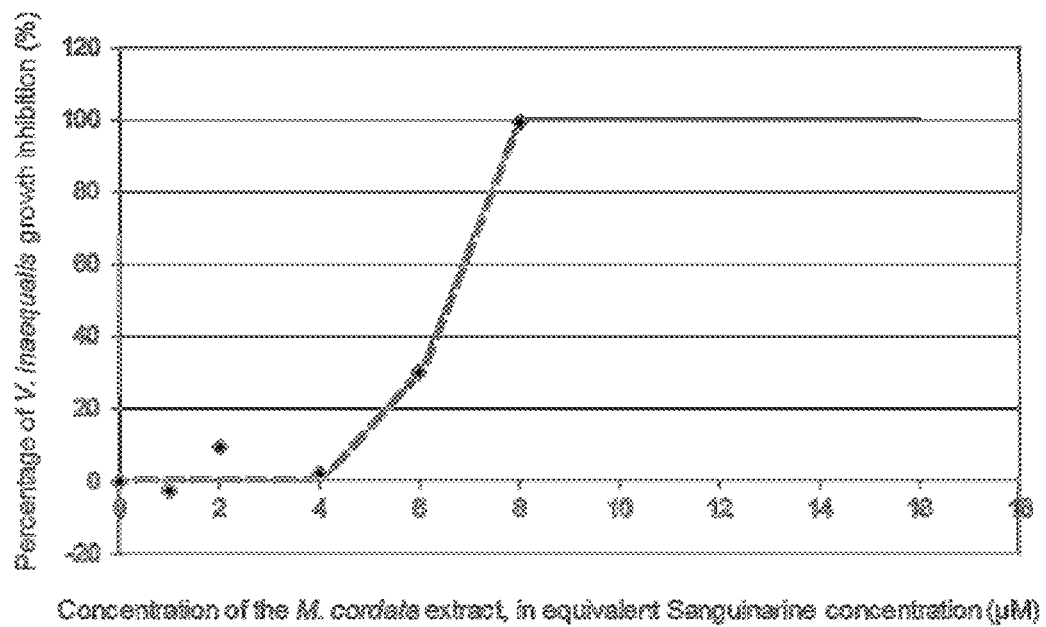
FIG. 7 is a growth curve describing the effect of increasing concentrations of *Macleaya cordata* extract on *Venturia inaequalis*, showing the non-fungistatic concentration of 5 µM, expressed in the equivalent sanguinarine concentration.

The results of the growth inhibition of *V. inaequalis* are presented in FIG. 7.

Example 7: In Planta Effects Against *Venturia inaequalis* of a Non-Fungicidal Amount of *Macleaya cordata* Crude Extract A crude extract of *Macleaya cordata* was diluted to a final concentration of 20 ppm and 5 ppm (corresponding to 8 ppm and 2 ppm of sanguinarine respectively).

The effect of spraying the diluted *Macleaya cordata* extract against *Venturia inaequalis* (apple scab) is assessed in planta on apple tree leaves, *Malus domestica*.

The antifungal effect is assessed by measuring the percentage of the fungal infection surface on the infected leaves. Spraying the leaves with water is used as a negative control treatment. However, given the differences among the infection rate among the apple tree rows, the effect was compared between the treated leaves and the overlying non-treated leaves of the same tree.

The treatment groups are as follows:
*M. cordata* extract (2 µM Sanguinarine equivalent) sprayed on to the leaves two days prior to their inoculation with *V. inaequalis*,
*M. cordata* extract (2 µM Sanguinarine equivalent) sprayed on to the leaves along with their inoculation with *V. inaequalis*,
*M. cordata* extract (2 µM Sanguinarine equivalent) sprayed on to the leaves two days after their inoculation with *V. inaequalis*,
Water sprayed on to the leaves two days prior to their inoculation with *V. inaequalis*.

Figure 8:
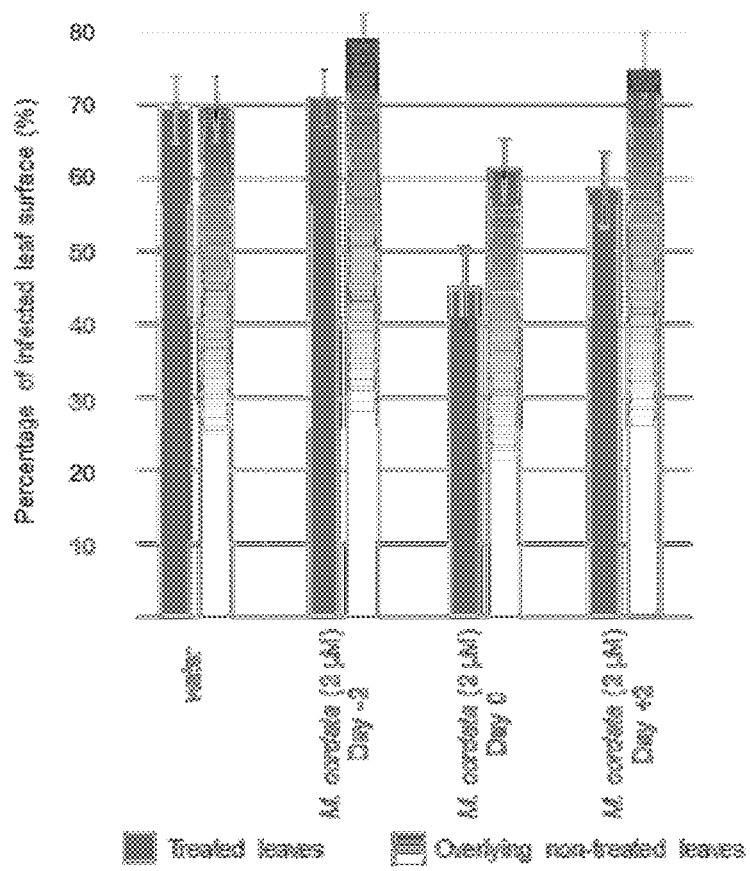
FIG. 8 is a graph showing the effects of the treatment of apple trees (*Malus domestica*) against apple scab (*Venturia inaequalis*) with a non-fungicidal amount of *Macleaya cordata* extract (2 µM, expressed in the equivalent sanguinarine concentration). The treatment groups are i) treatment with the *Macleaya cordata* extract two days prior to the fungal inoculation ii) treatment with the *Macleaya cordata* extract simultaneously with the inoculation and iii) treatment with the *Macleaya cordata* extract two days past the fungal inoculation. The antifungal effects are calculated on the basis of the percentage of the treated infected leaf surface. The results are compared with the percentage of the infected leaf surface of the corresponding non-treated overlying leaves. A control group of apple trees is treated with water.

The percentage of infected leaves was counted 21 days past their inoculation with *V. inaequalis*. The results are presented in FIG. 8.

Applying a treatment having a sanguinarine at the non-fungicide concentration of 2 prior, simultaneously or after the inoculation with *V. inaequalis*, showed a considerable re decrease in the infected surface of the treated leaves according to the present method. The treatment of apple tree leaves with the association of *M. cordata* extract and the plant defense molecule elicitor (SDP) Bion® (acibenzolar-S-methyl, Sygenta, 400 ppm) is currently undergoing.

The invention claimed is:

1. A method for controlling or treating a fungal infection by a phytopathogenic fungal strain on a plant organ, said method comprising the steps of:
   i) in vitro determining the non-fungicidal concentration of at least one potentiating agent of a plant defense molecule selected from the group consisting of chelerythrine, sanguinarine; and Cl$^-$, HSO$_4^-$, I$^-$, HCO$_3^-$ salts thereof, against the phytopathogenic fungal strain; said determination being carried out by comparing the growth of the phytopathogenic fungal strain cultures in contact with increasing concentrations of said at least one potentiating agent of a plant defense molecule, with the growth of a control culture of the phytopathogenic fungal strain, in the absence of said at least one potentiating agent of a plant defense molecule; the last concentration of the increasing concentrations of the at least one potentiating agent of a plant defense molecule resulting in the same fungal culture growth as the control culture being retained as the non-fungicidal concentration of said at least one potentiating agent of a plant defense molecule; then
   ii) applying on the plant organ a composition comprising said at least one potentiating agent of a plant defense molecule in the determined non-fungicidal concentration, such that the amount applied is a potentiating amount but is not an amount that is fungicidal per se, in association with a phytopharmaceutical vehicle.

2. The method according to claim 1, wherein said in vitro determination of the non-fungicidal amount of at least one potentiating agent of a plant defense molecule is carried-out by spectrophotometry or nephelometry.

3. The method according to claim 1, wherein said phytopathogenic fungal infection is an infection by a phytopathogenic fungus selected from the group consisting of the genera *Alternaria, Sclerotinia* and *Venturia*.

4. The method according to claim 1, wherein said fungal infection is an infection by a phytopathogenic fungus selected from the group consisting of *Alternaria brassicicola, Alternaria dauci* and *Ventuna inaequalis*.

5. The method according to claim 1, wherein the plant is selected from the group consisting of plants of the Brassicacae, Apiaceae, Vitaceae and Rosaceae families.

6. The method according to claim 1, wherein the plant is selected from the group consisting of *Brassica carinata, Brassica juncea, Brassica oleracea, Brassica napus, Brassica nigra* and *Brassica rapa*.

7. The method according to claim 1, wherein the plant is selected from the group consisting of *Brassica oleracea, Daucus carota* subsp. *Sativa* and *Malus domestica*.

8. The method according to claim 1, wherein the plant organ, the phytopathogenic fungus and the non-fungicidal concentration of the at least one potentiating agent of a plant defense molecule in the applied composition is selected from the following combinations:
   a. said plant organ belonging to a plant of the Brassicaceae family, said phytopathogenic fungus being a strain of the *Alternaria* genus, and said non-fungicidal concentration of the at least one potentiating agent of a plant defense molecule in the applied composition being from 1 to 25 µM; or
   b. said plant organ belonging to a plant of the Apiaceae family, said phytopathogenic fungus being a strain of the *Alternaria* genus, and said non-fungicidal concentration of the at least one potentiating agent of a plant defense molecule in the applied composition being from 1 to 10 µM; or
   c. said plant organ belonging to a plant of the Rosaceae family, said phytopathogenic fungus being a strain of the *Venturia* genus, and said non-fungicidal concentration of the at least one potentiating agent of a plant defense molecule in the applied composition being from 1 to 5 µm.

9. The method according to claim 1, wherein the plant organ, the phytopathogenic fungus and the non-fungicidal concentration of the at least one potentiating agent of a plant defense molecule in the applied composition is selected from the following combinations:
   a. said plant organ belonging to a plant of the Brassicaceae family plant, said phytopathogenic fungus being *Alternaria brassicicola*, and said non-fungicidal concentration of the at least one potentiating agent of a plant defense molecule in the applied composition being from 1 to 25 µM; or
   b. said plant organ belonging to the *Daucus carota* plant, said phytopathogenic fungus being *Alternaria dauci*, and said non-fungicidal concentration of the at least one potentiating agent of a plant defense molecule in the applied composition being from 1 to 10 µM; or c. said plant organ belonging to the *Malus domestica* plant, said phytopathogenic fungus being *Venturia inaequalis*, and said non-fungicidal concentration of the at least one potentiating agent of a plant defense molecule in the applied composition being from 1 to 5 μm.

10. The method according to claim 1, wherein said plant organ belongs to *Brassica oleracea* plant, said phytopathogenic fungus being *Alternaria brassicicola*, and said non-fungicidal concentration of the at least one potentiating agent of a plant defense molecule in the applied composition being from 1 to 25 μM.

11. The method according to claim 1, wherein the composition further comprises a plant defense molecule selected from the group consisting of brassinin, camalexin, resveratrol, 3,5-dihydroxybiphenyl, aucuparin and 6-methoxymellein.

12. The method according to claim 1, wherein the composition further comprises an agent for stimulating the production of a plant defense molecule.

13. The method according to claim 1, wherein the composition further comprises at least one agent for stimulating the production of a plant defense molecule; said agent being selected from the group consisting of acibenzolar-S-methyl, chitosan, laminarin, *Reynoutria Sachalinensis* extract, calcium prohexadione, harpine, yeast wall extracts, oligogalacturonides and calcium phosphite.

14. The method according to claim 1, wherein the composition further comprises an insecticide and/or a herbicide.

* * * * *